(12) United States Patent
Giambattista et al.

(10) Patent No.: US 10,518,029 B2
(45) Date of Patent: Dec. 31, 2019

(54) INFUSION DEVICE

(71) Applicant: CAREBAY EUROPE LTD, Sliema (MT)

(72) Inventors: Lucio Giambattista, Lighthouse Point, FL (US); Antonio Bendek, Wellington, FL (US)

(73) Assignee: SHL MEDICAL AG, Zug (CH)

( * ) Notice: Subject to any disclaimer, the term of this patent is extended or adjusted under 35 U.S.C. 154(b) by 0 days.

(21) Appl. No.: 15/989,516

(22) Filed: May 25, 2018

(65) Prior Publication Data
US 2018/0289889 A1 Oct. 11, 2018

Related U.S. Application Data

(63) Continuation of application No. 14/391,947, filed as application No. PCT/EP2013/057326 on Apr. 8, 2013, now Pat. No. 10,251,995.
(Continued)

(30) Foreign Application Priority Data

Apr. 10, 2012 (SE) ...................................... 1250358

(51) Int. Cl.
*A61M 5/145* (2006.01)
*A61M 5/158* (2006.01)
(Continued)

(52) U.S. Cl.
CPC ...... *A61M 5/1454* (2013.01); *A61M 5/14566* (2013.01); *A61M 5/158* (2013.01);
(Continued)

(58) Field of Classification Search
CPC ........... A61M 2005/14252; A61M 2005/1583; A61M 2005/1585; A61M 2005/31518;
(Continued)

(56) References Cited

U.S. PATENT DOCUMENTS 6,599,272 B1 * 7/2003 Hjertman ............... A61M 5/315
604/209
2002/0007154 A1 1/2002 Hansen et al.
(Continued)

FOREIGN PATENT DOCUMENTS

WO 98/10914 A1 3/1998
WO 01/19434 A1 3/2001
(Continued)

OTHER PUBLICATIONS

EPO, Int'l Search Report in PCT/EP2013/057326, dated Sep. 30, 2013.
EPO, Written Opinion in PCT/EP2013/057326, dated Sep. 30, 2013.

*Primary Examiner* — Brandy S Lee
(74) *Attorney, Agent, or Firm* — McDonnell Boehnen Hulbert & Berghoff LLP

(57) ABSTRACT

The present invention relates to an infusion device comprising a housing; a compartment inside said housing for positioning a medicament container, an infusion needle arranged to said housing, being connectable to said medicament container for delivering a dose of medicament, a piston plunger arranged in said housing capable of acting on said medicament container for delivering a dose of medicament, mechanical drive means capable of acting on said piston plunger for delivering a dose of medicament. The invention is characterised in that said piston plunger comprises a number of distinct segments being inter-connectable to each other for forming an elongated piston plunger.

8 Claims, 29 Drawing Sheets

Related U.S. Application Data

(60) Provisional application No. 61/622,252, filed on Apr. 10, 2012.

(51) Int. Cl.
 *A61M 5/315* (2006.01)
 *A61M 5/142* (2006.01)

(52) U.S. Cl.
 CPC ....... *A61M 5/1452* (2013.01); *A61M 5/14248* (2013.01); *A61M 2005/14252* (2013.01); *A61M 2005/1583* (2013.01); *A61M 2005/1585* (2013.01); *A61M 2005/31518* (2013.01)

(58) Field of Classification Search
 CPC ............ A61M 5/14248; A61M 5/1452; A61M 5/1454; A61M 5/14566; A61M 5/158
 See application file for complete search history.

(56) References Cited

U.S. PATENT DOCUMENTS

| | | | |
|---|---|---|---|
| 2007/0073236 A1* | 3/2007 | Mernoe | A61M 5/14244 604/151 |
| 2009/0124996 A1* | 5/2009 | Heneveld | A61F 2/0059 604/506 |
| 2011/0077595 A1 | 3/2011 | Eich et al. | |
| 2012/0078216 A1* | 3/2012 | Smith | A61M 5/145 604/500 |
| 2014/0088515 A1 | 3/2014 | Karlsson | |

FOREIGN PATENT DOCUMENTS

| | | |
|---|---|---|
| WO | 01/078812 A1 | 10/2001 |
| WO | 02/028455 A1 | 4/2002 |
| WO | 2004/056411 A2 | 7/2004 |
| WO | 2010/112377 A1 | 10/2010 |

\* cited by examiner

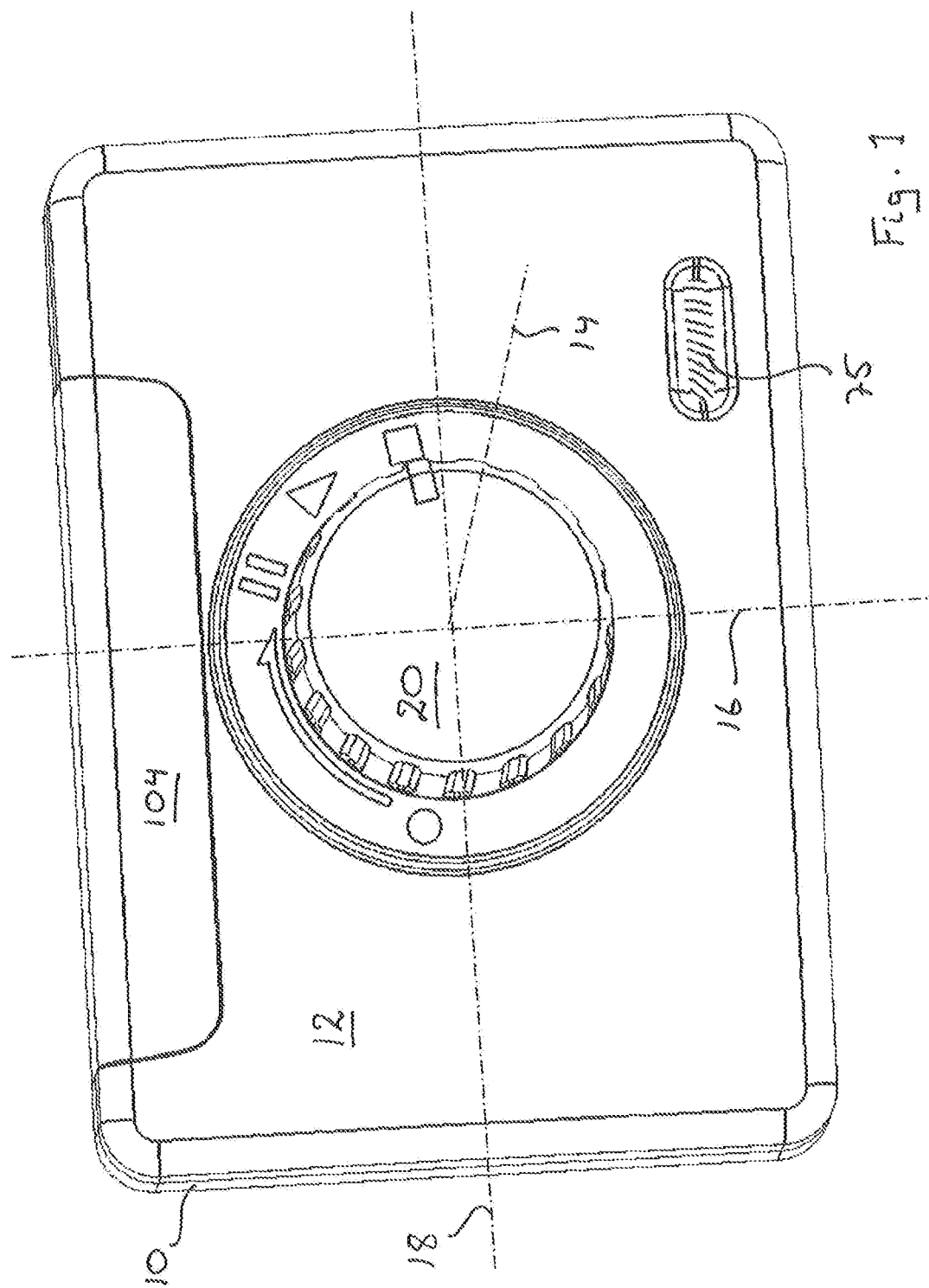

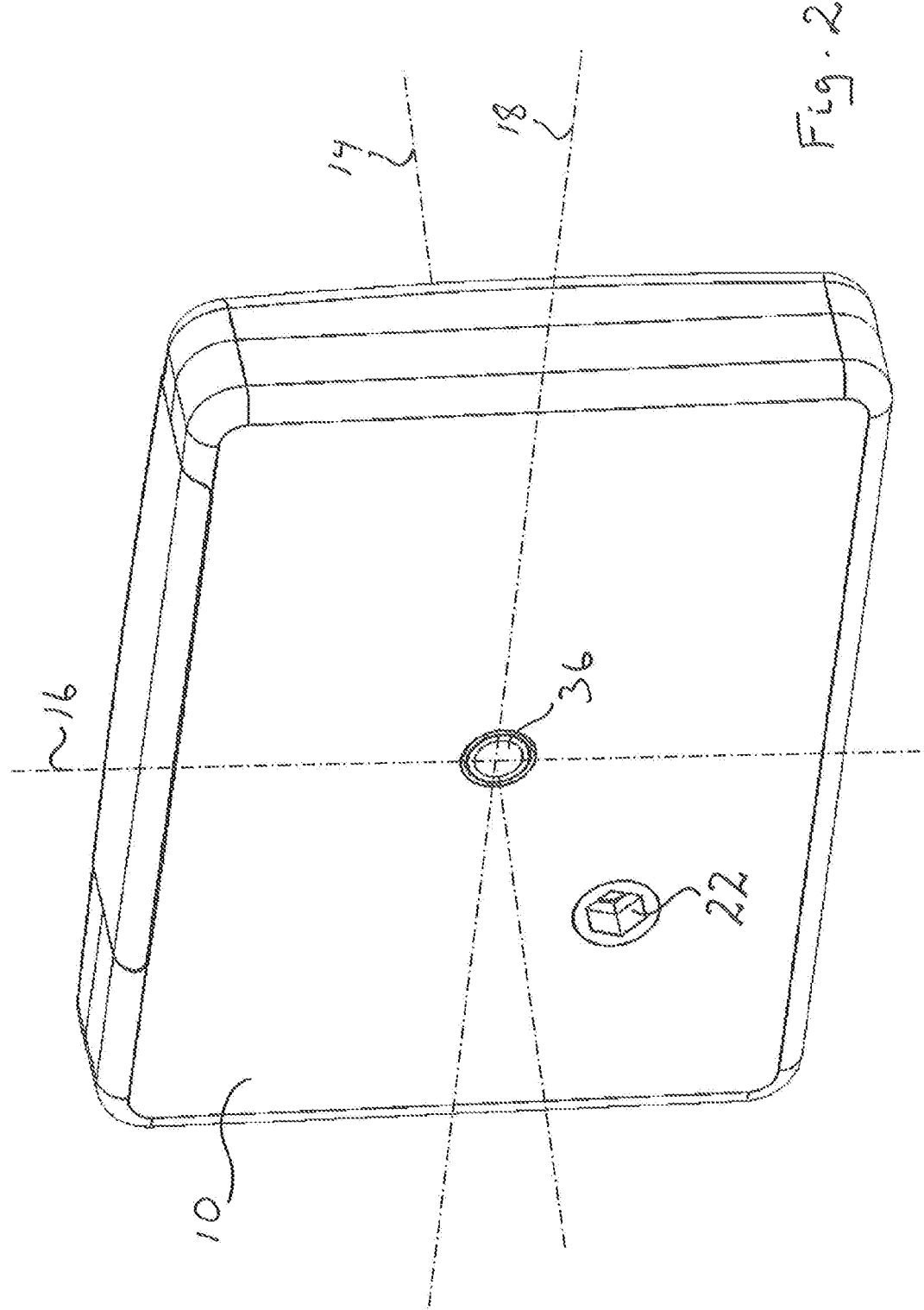

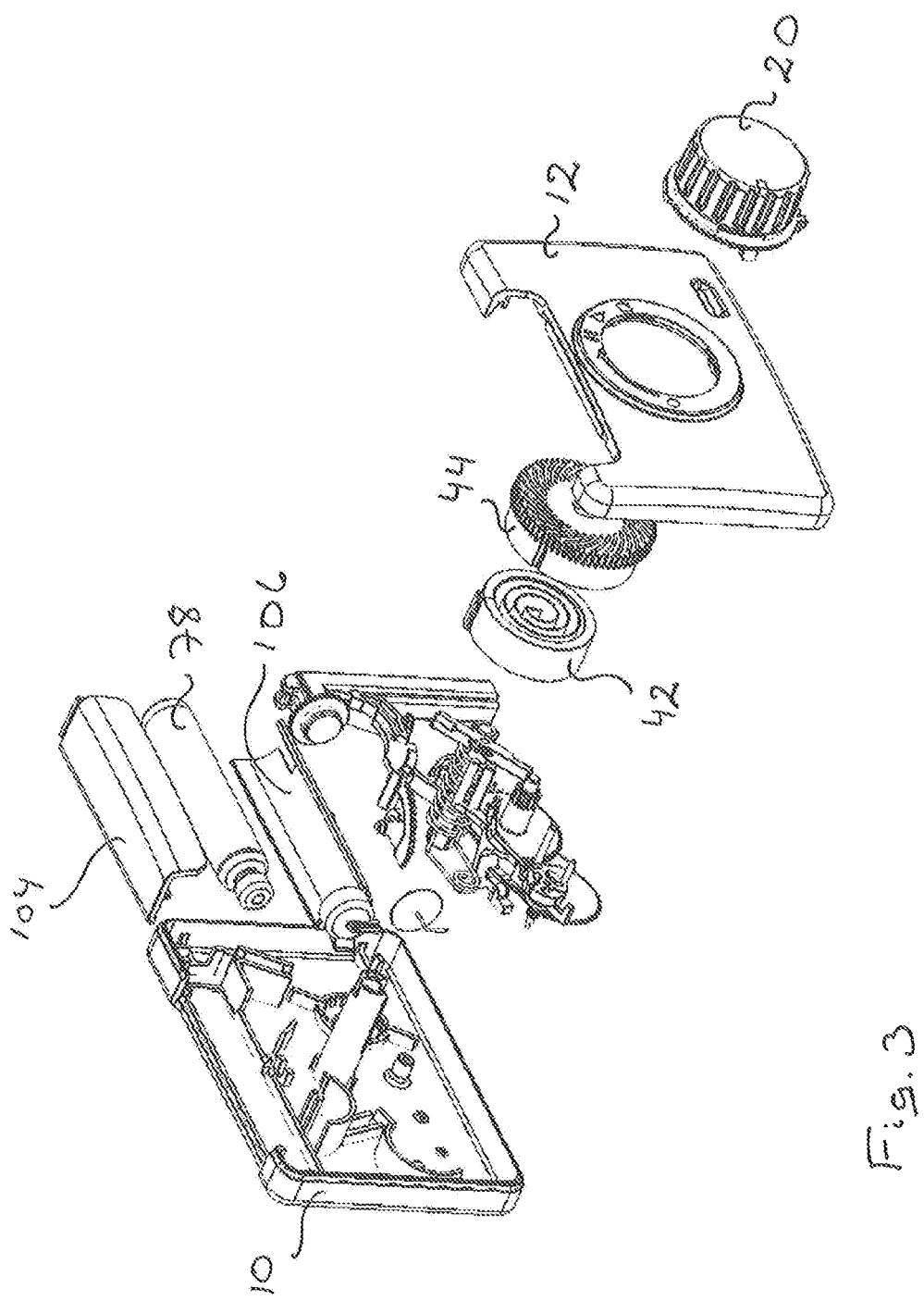

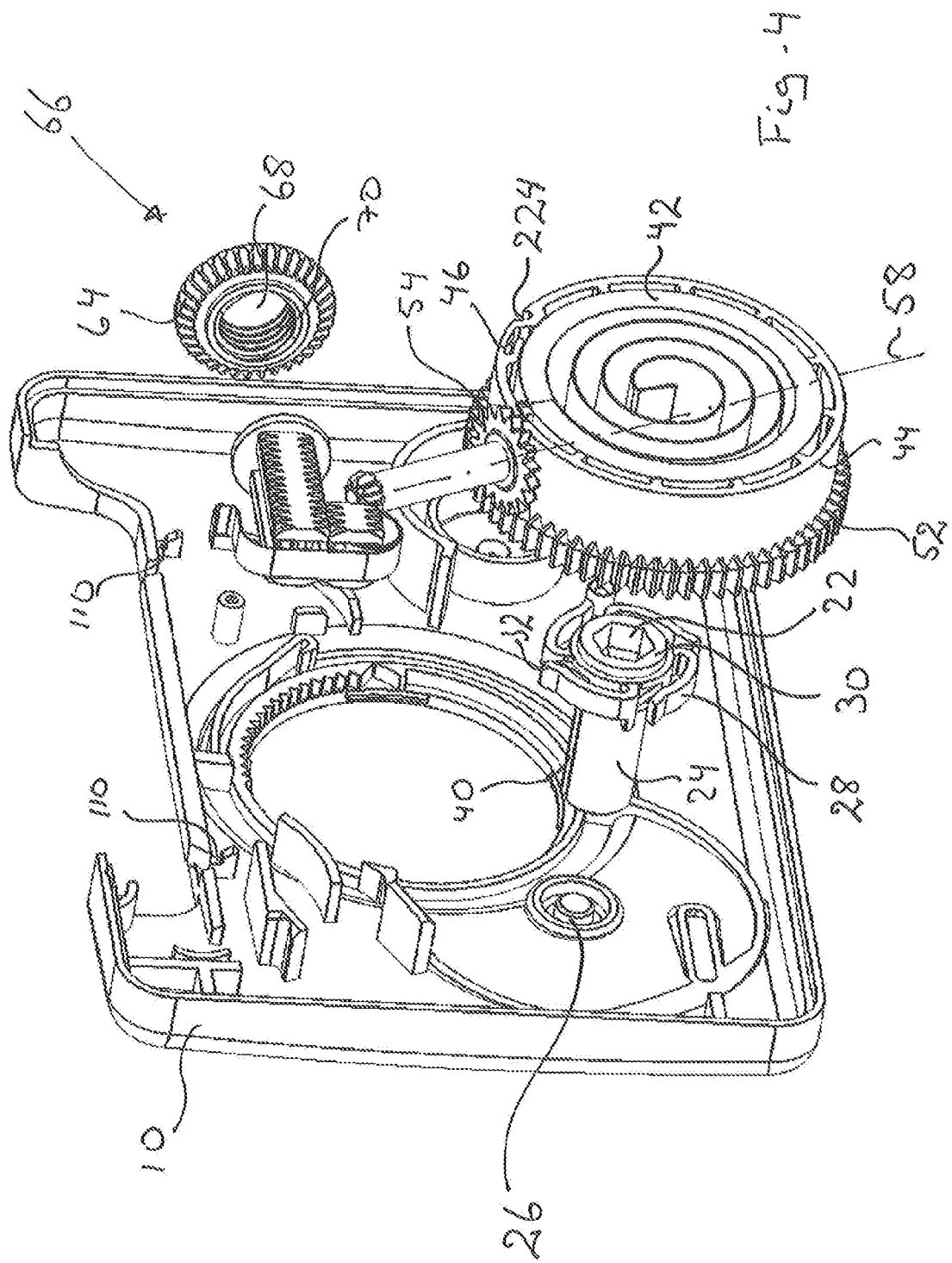

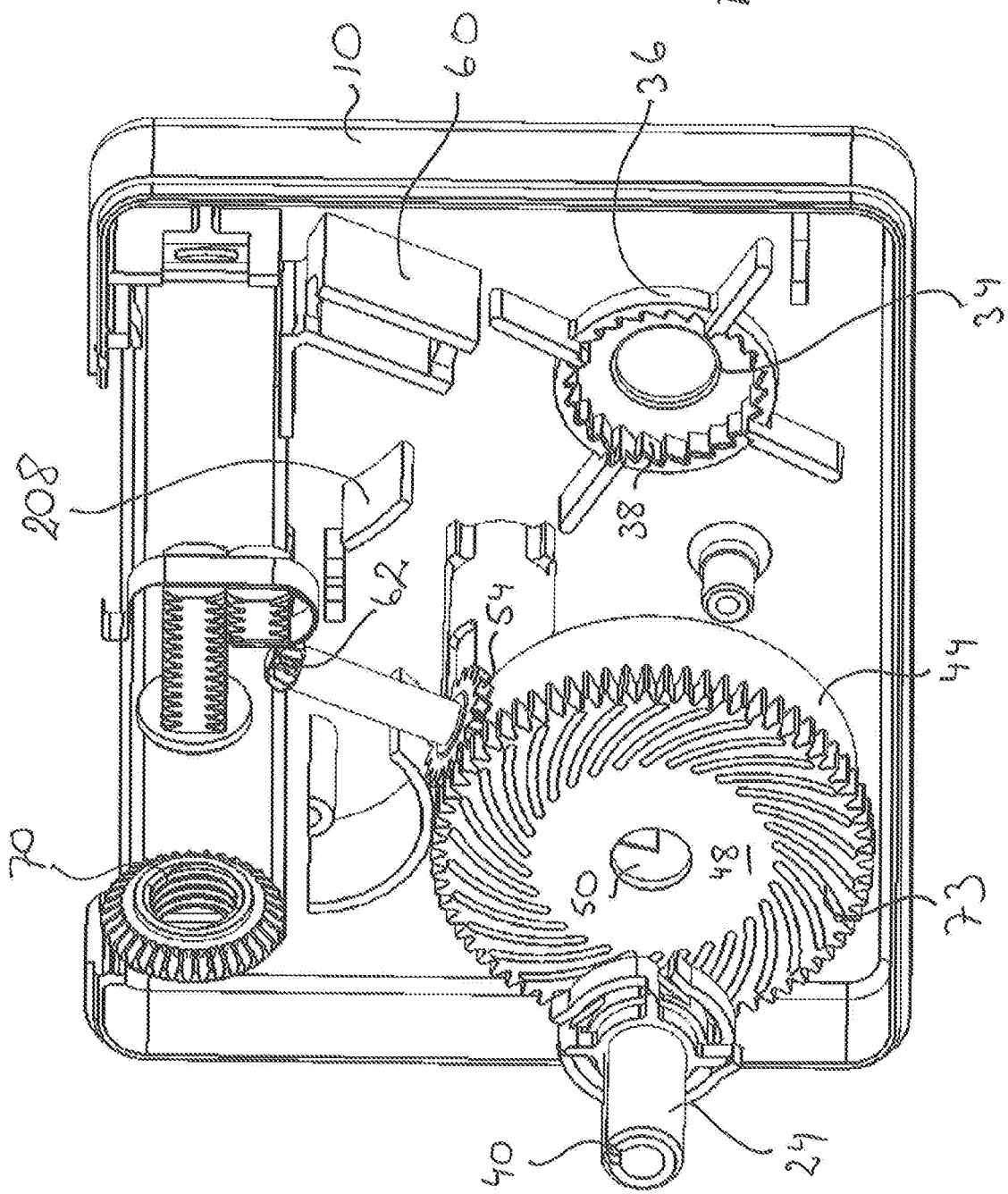

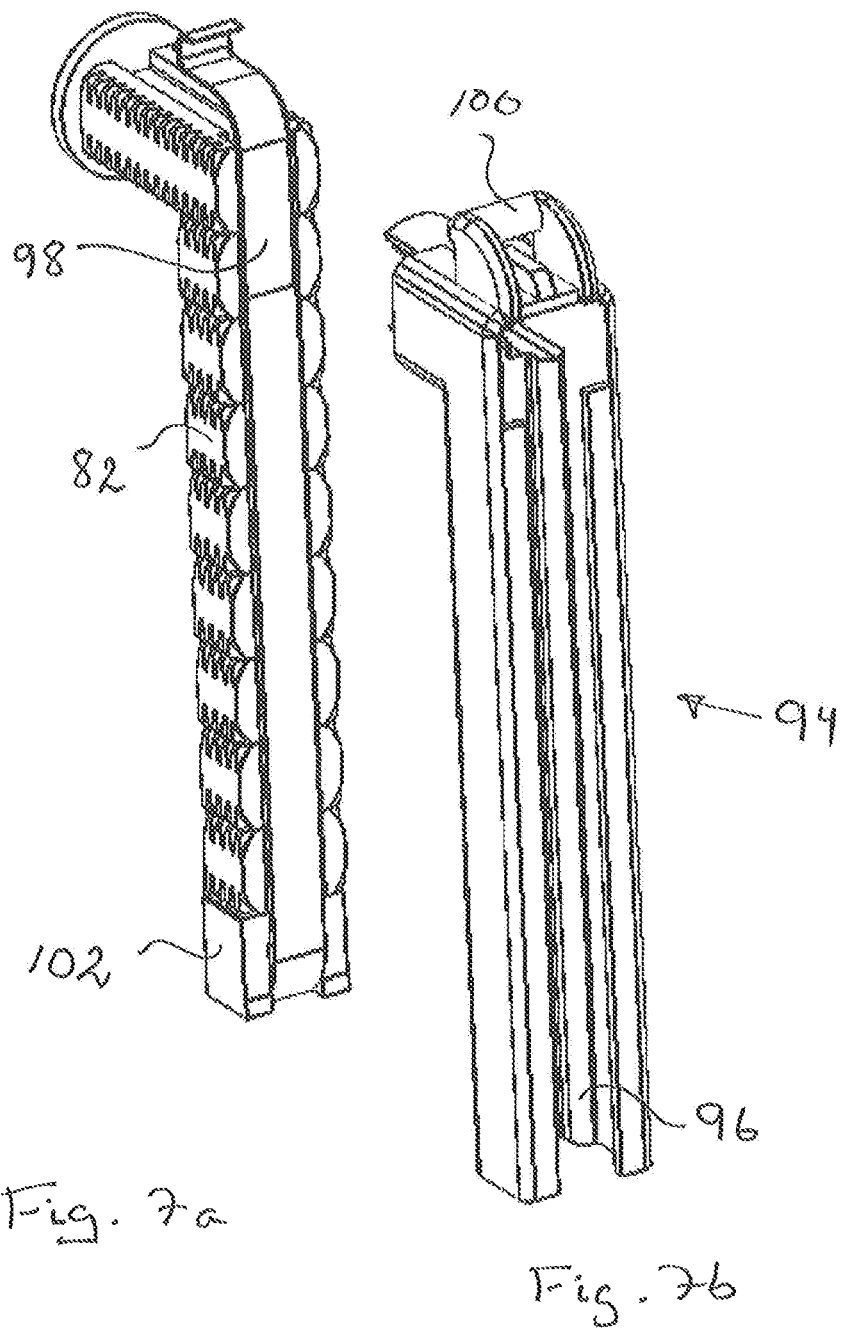

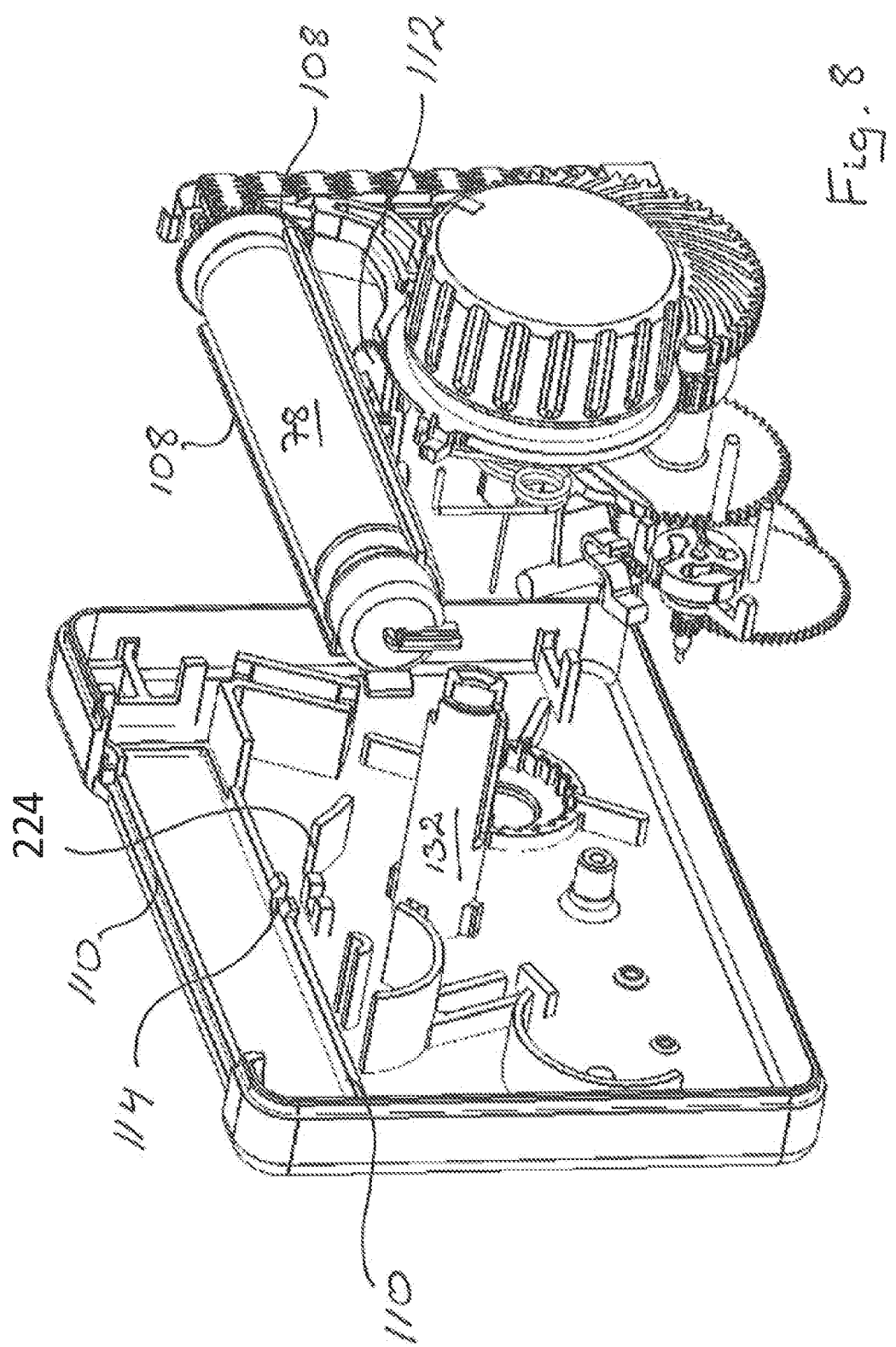

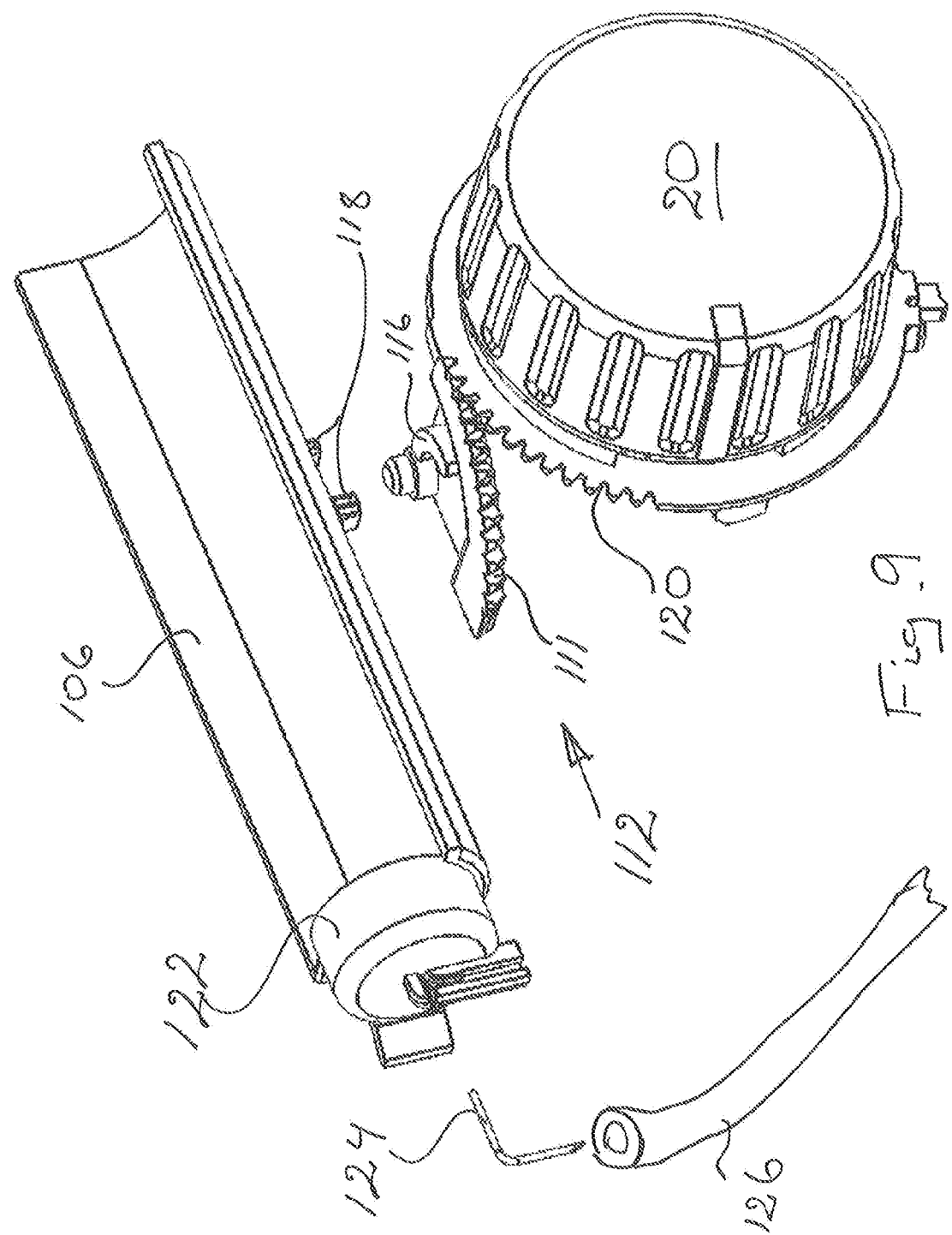

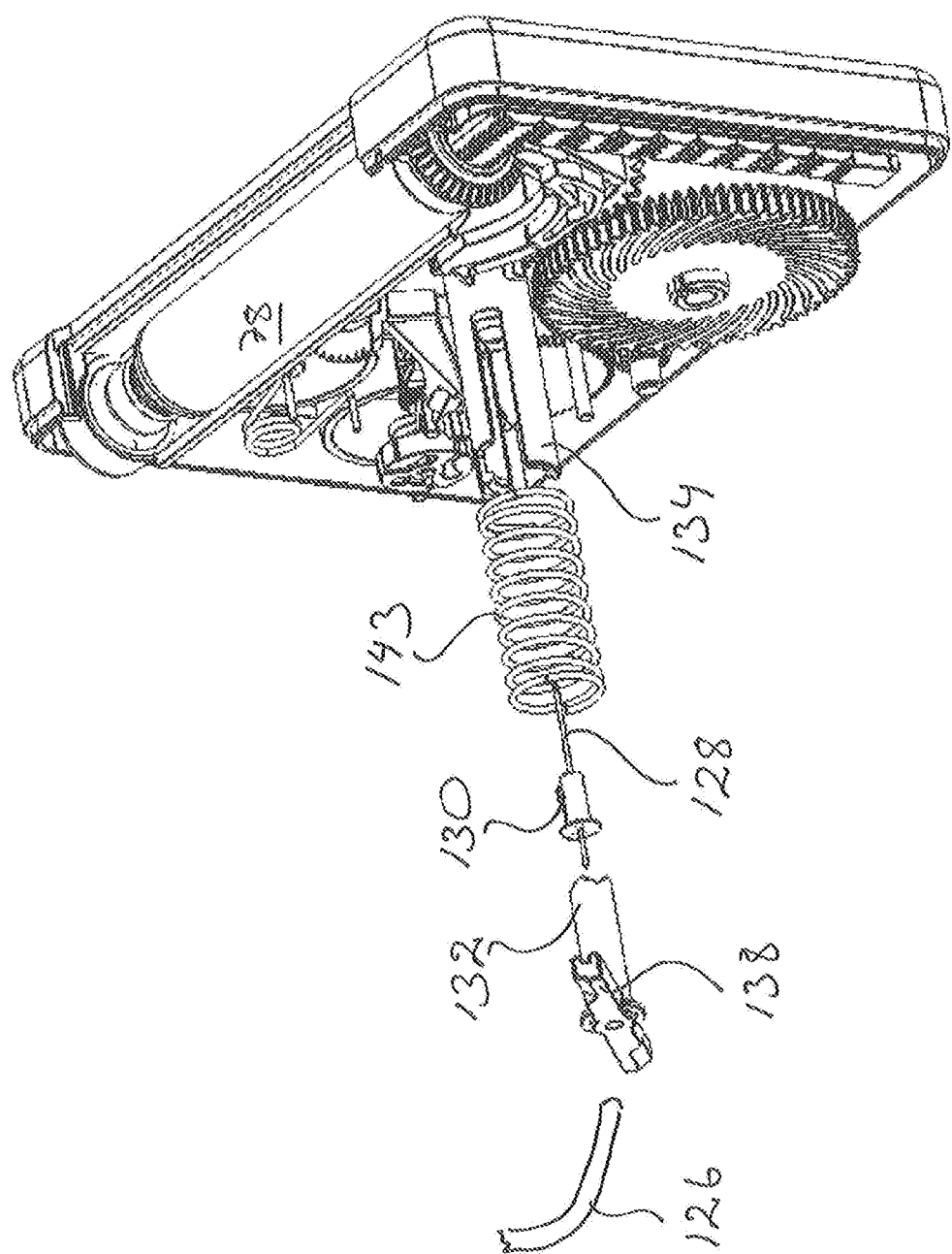

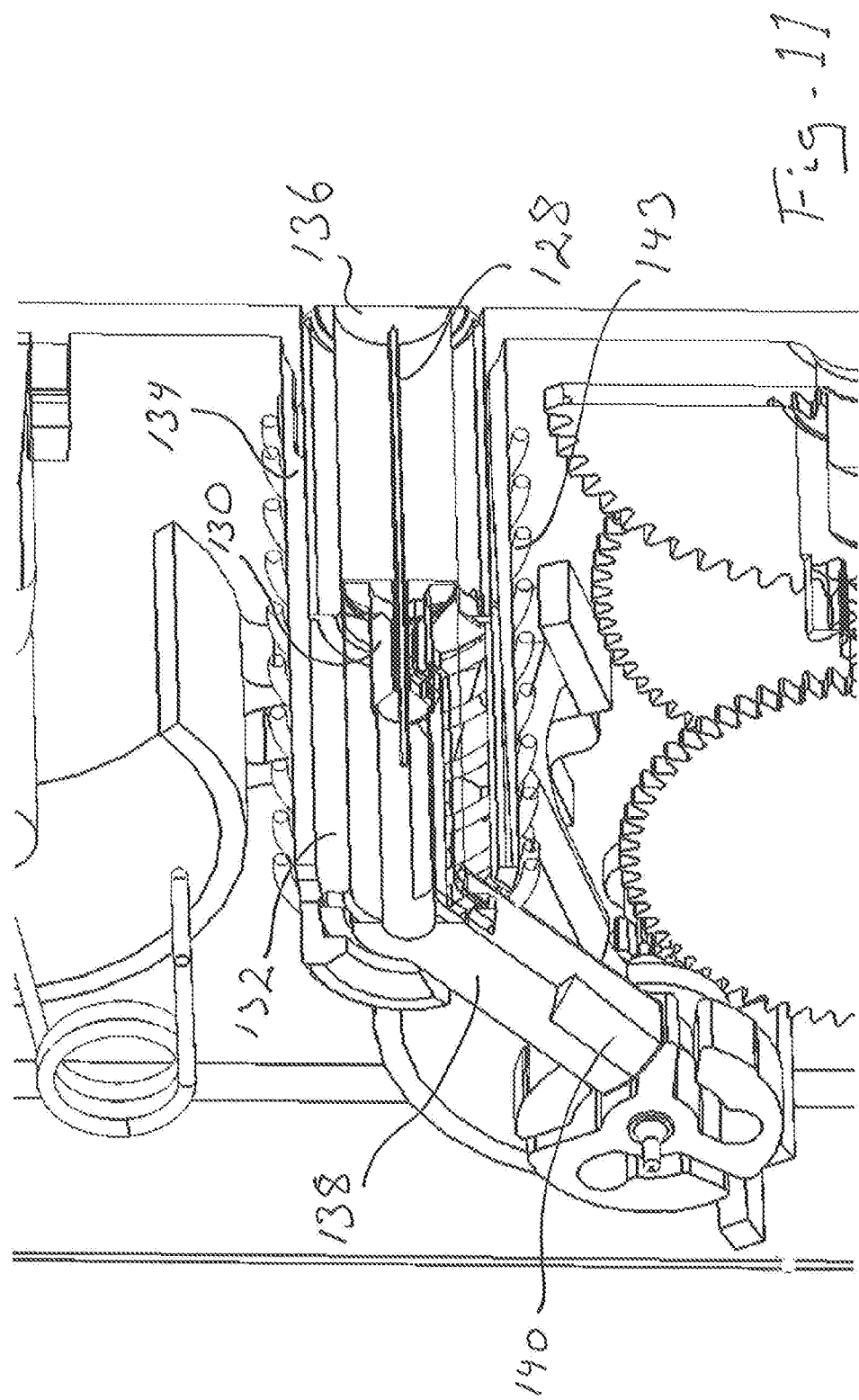

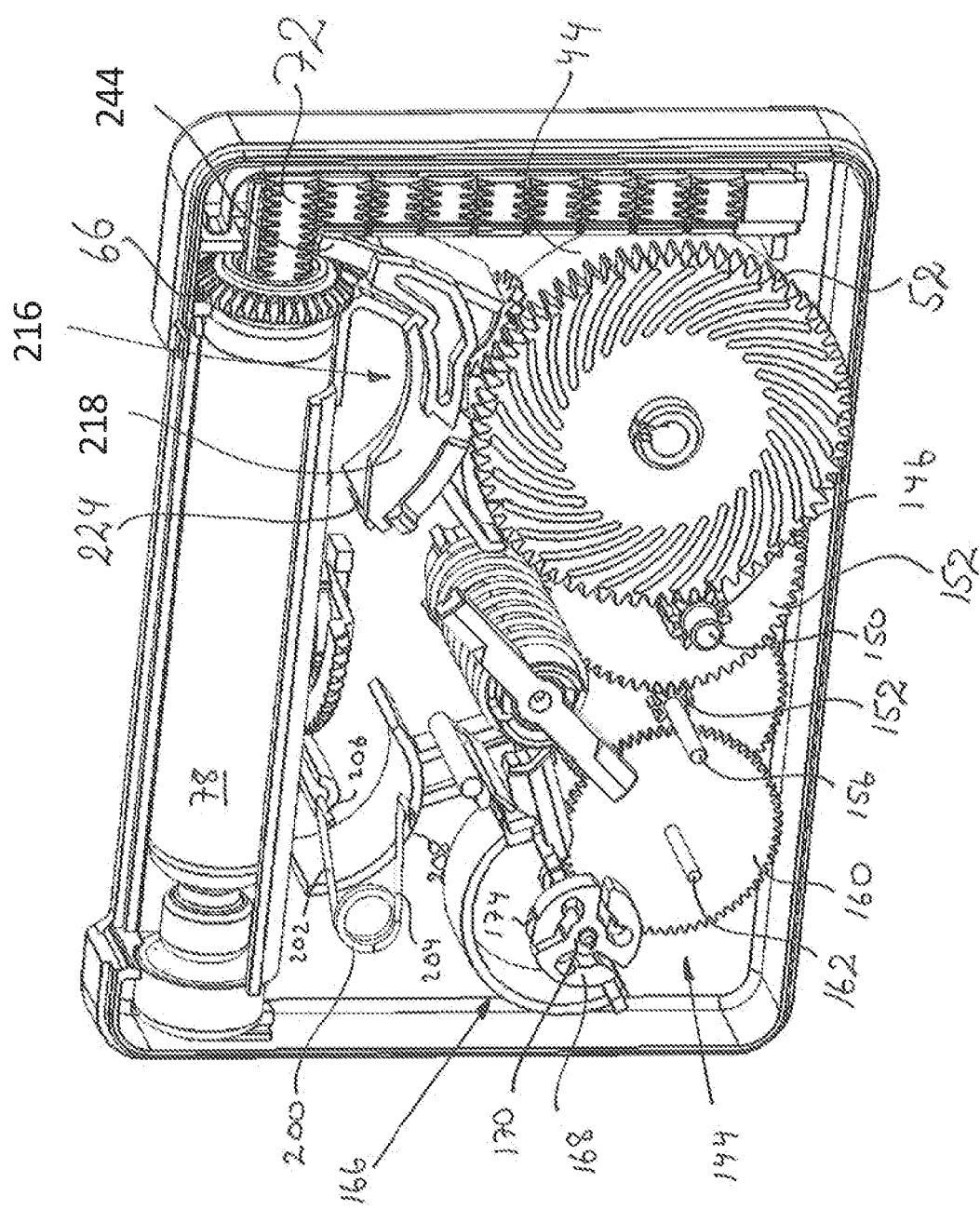

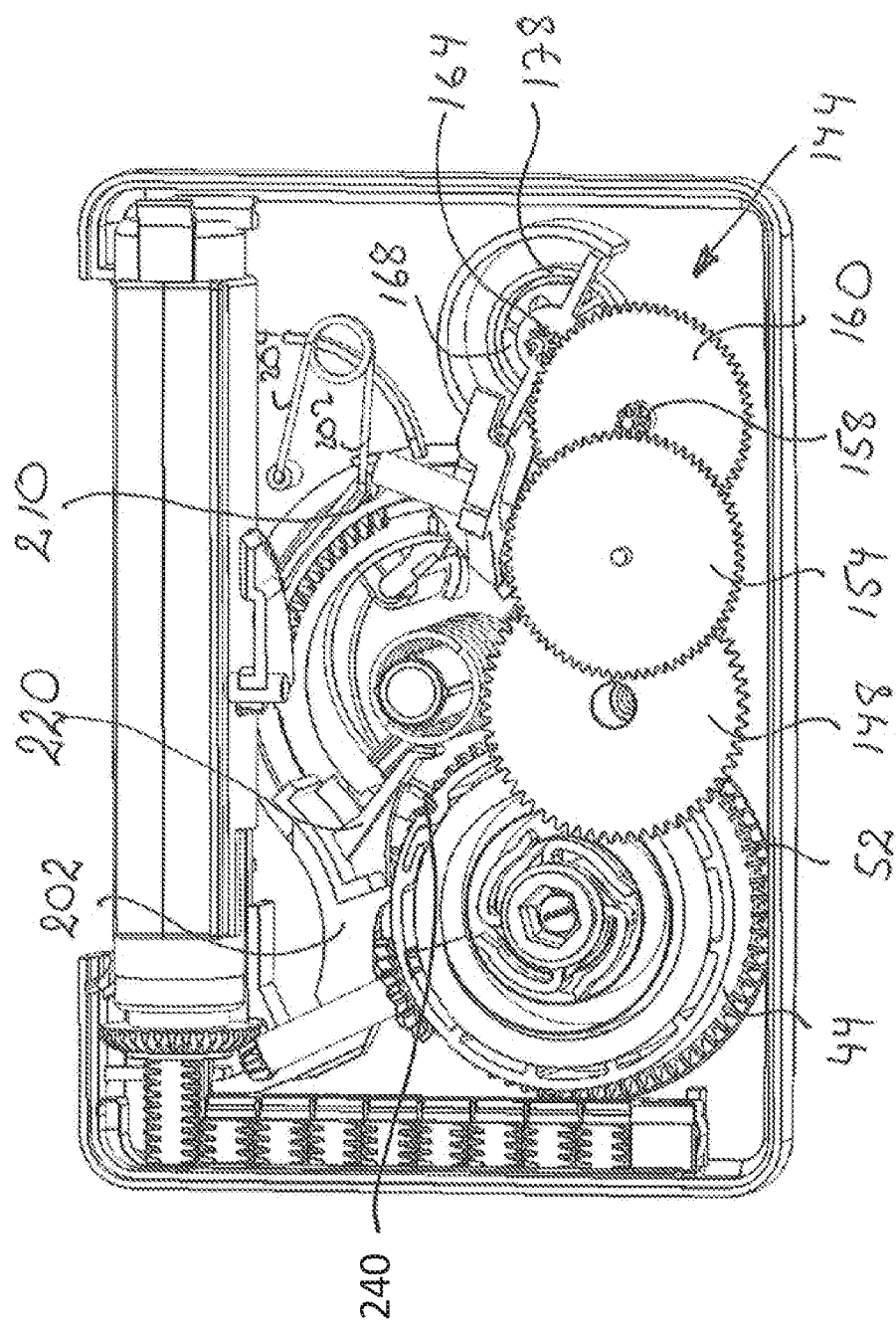

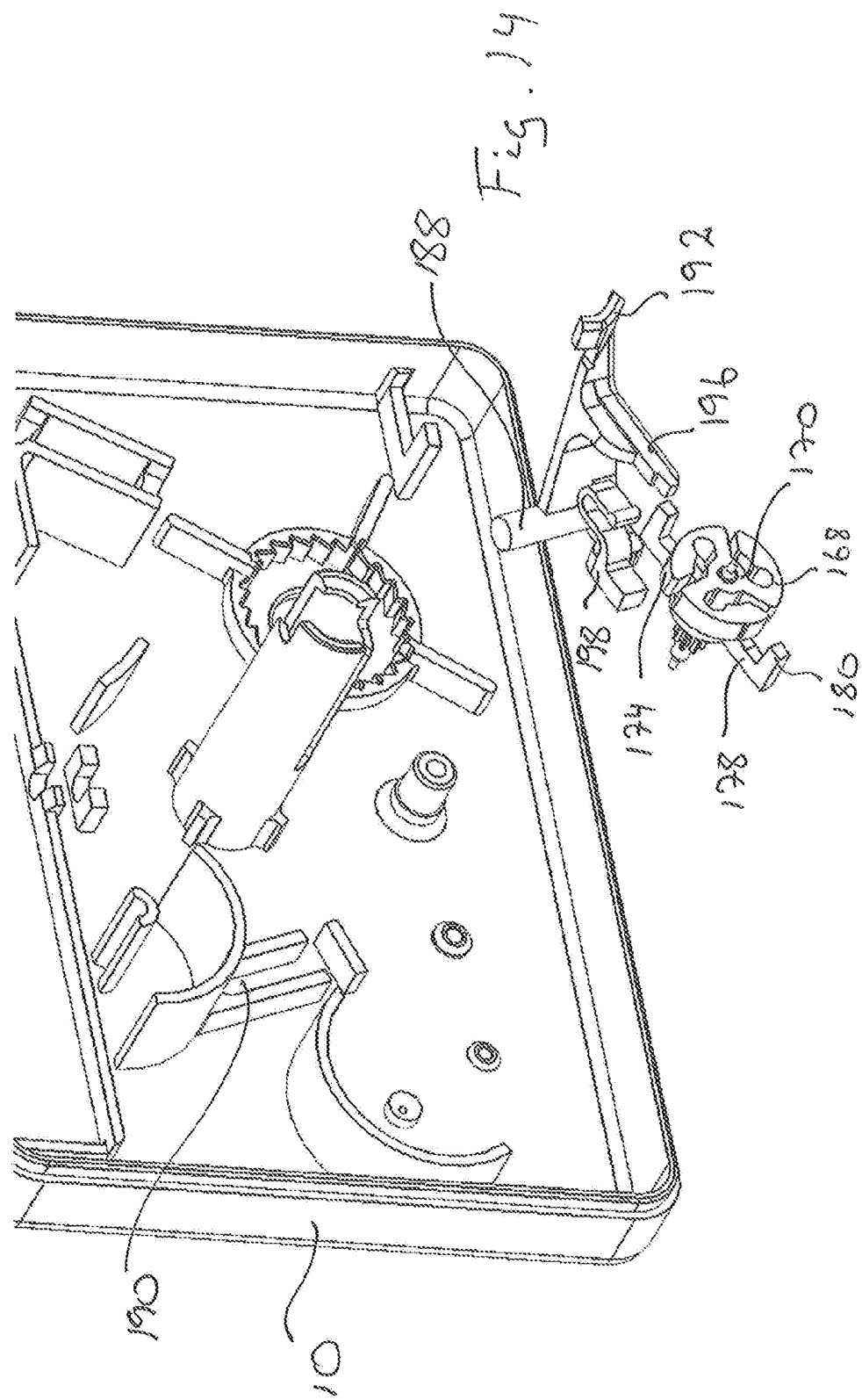

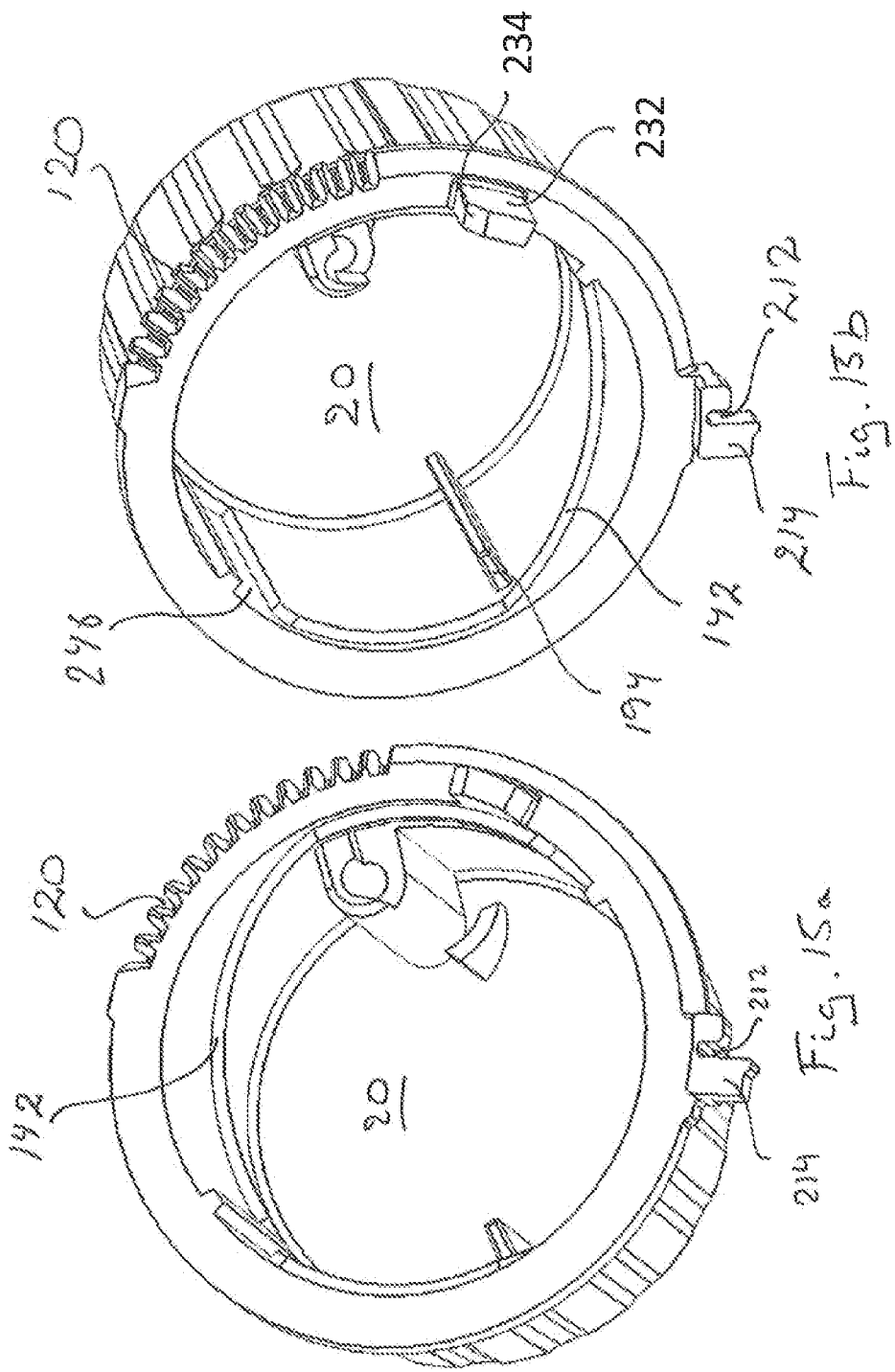

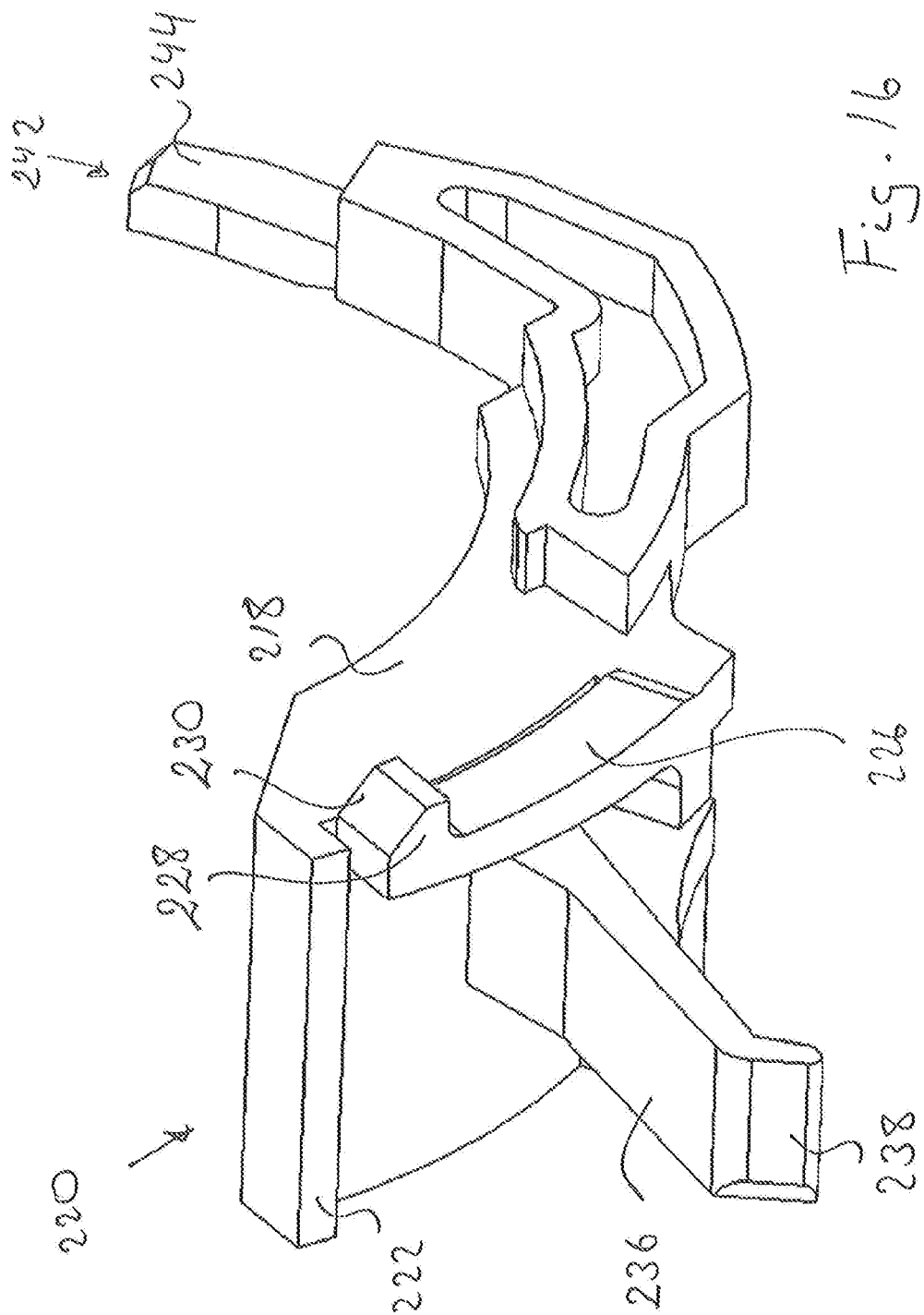

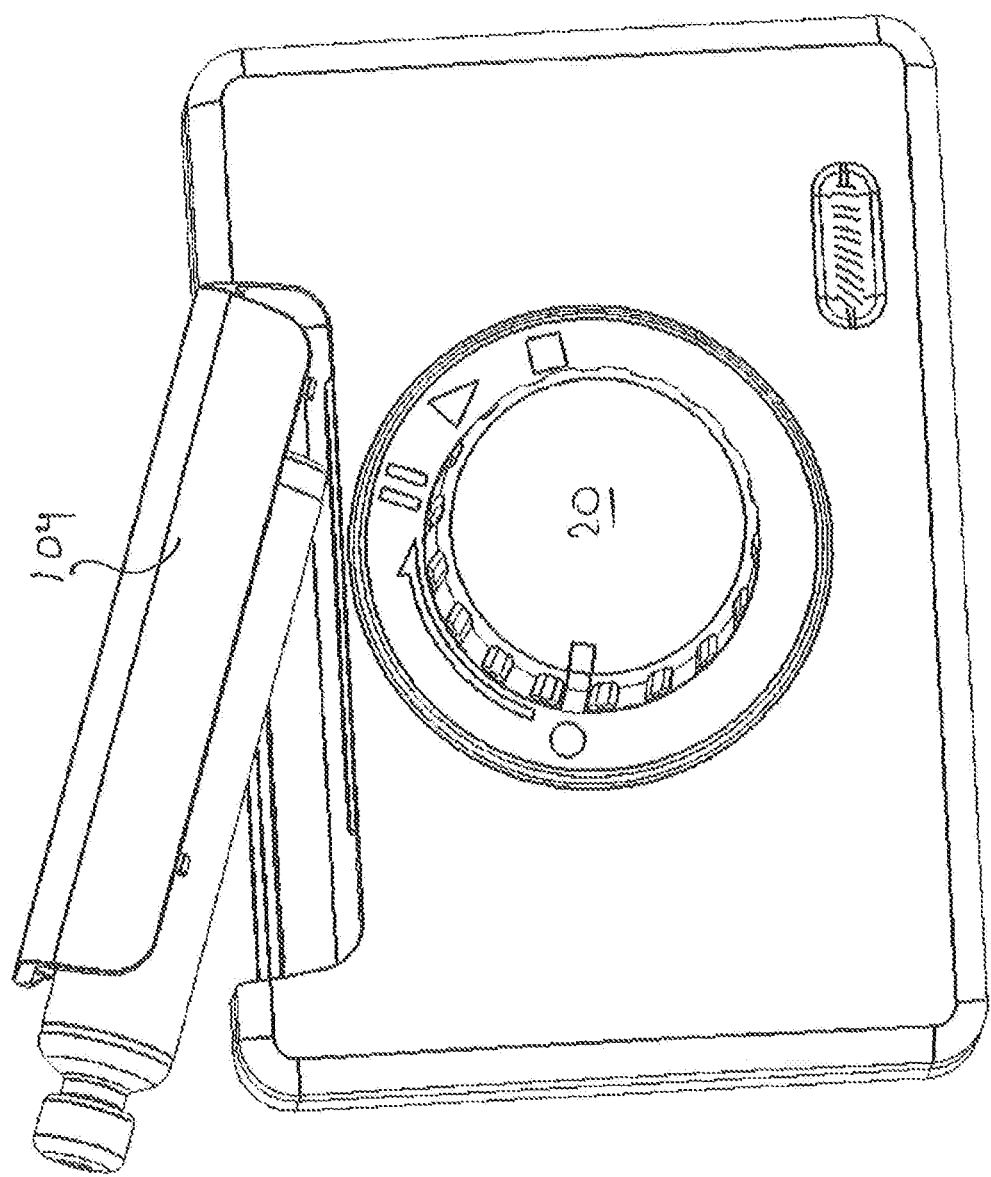

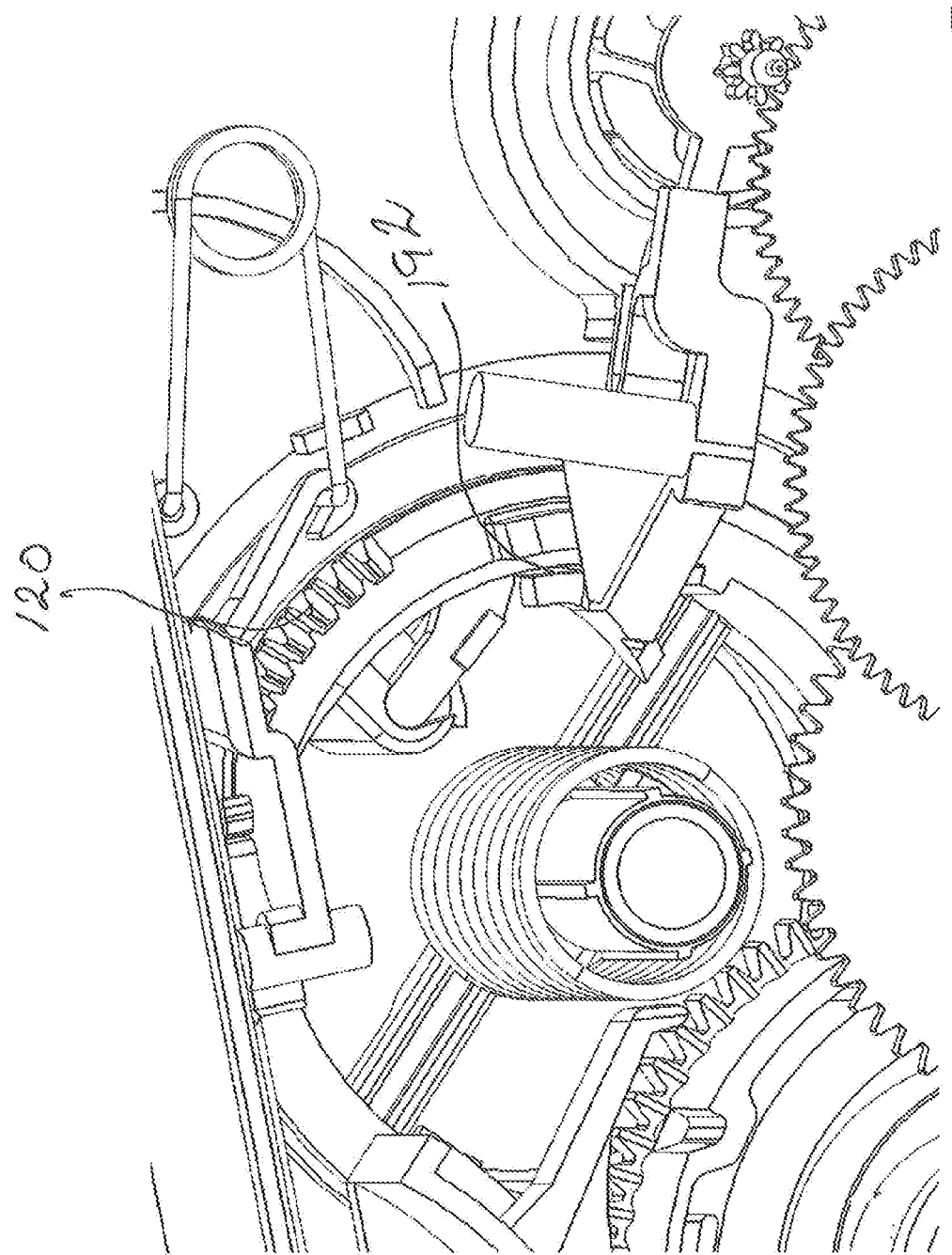

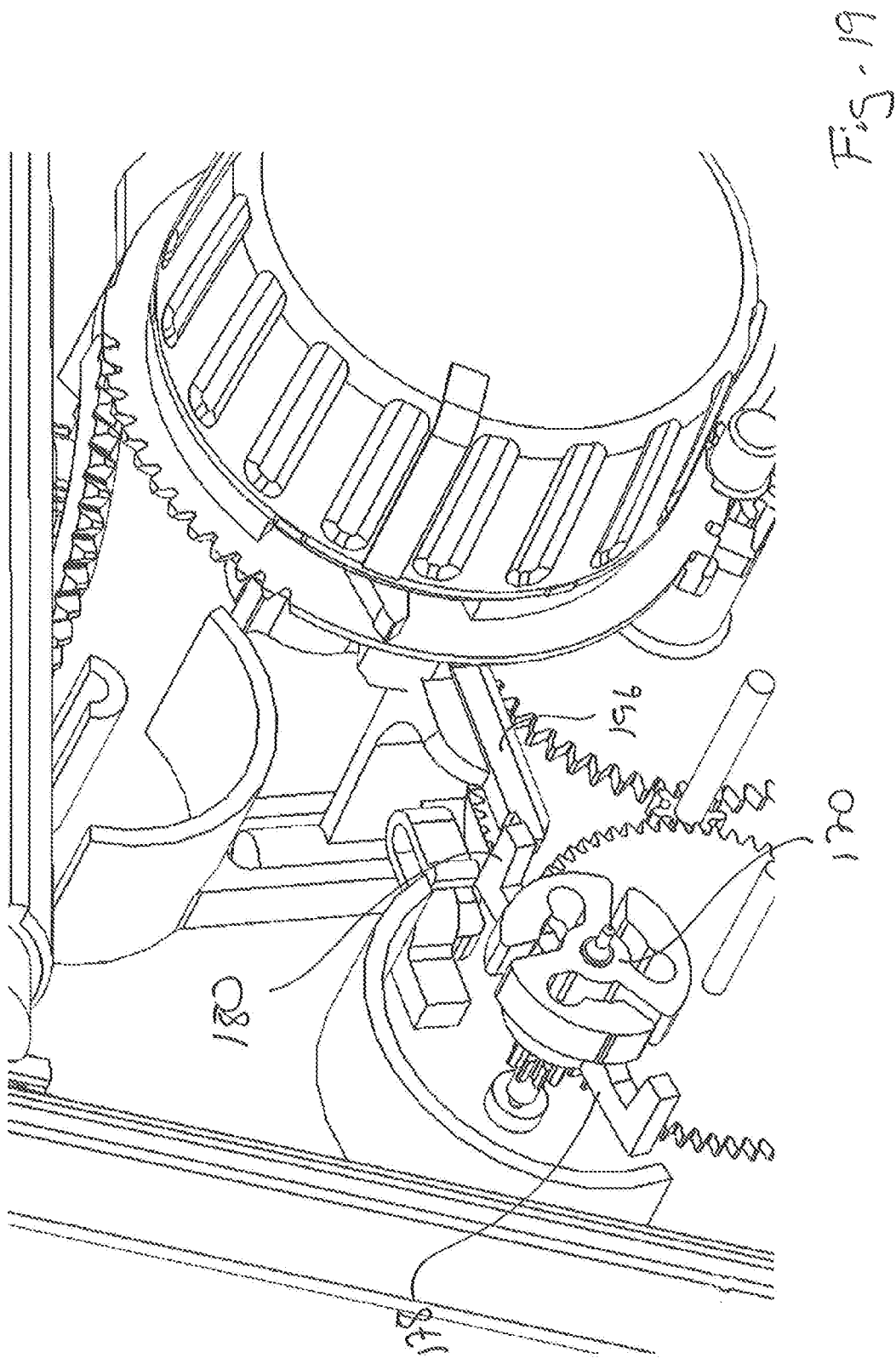

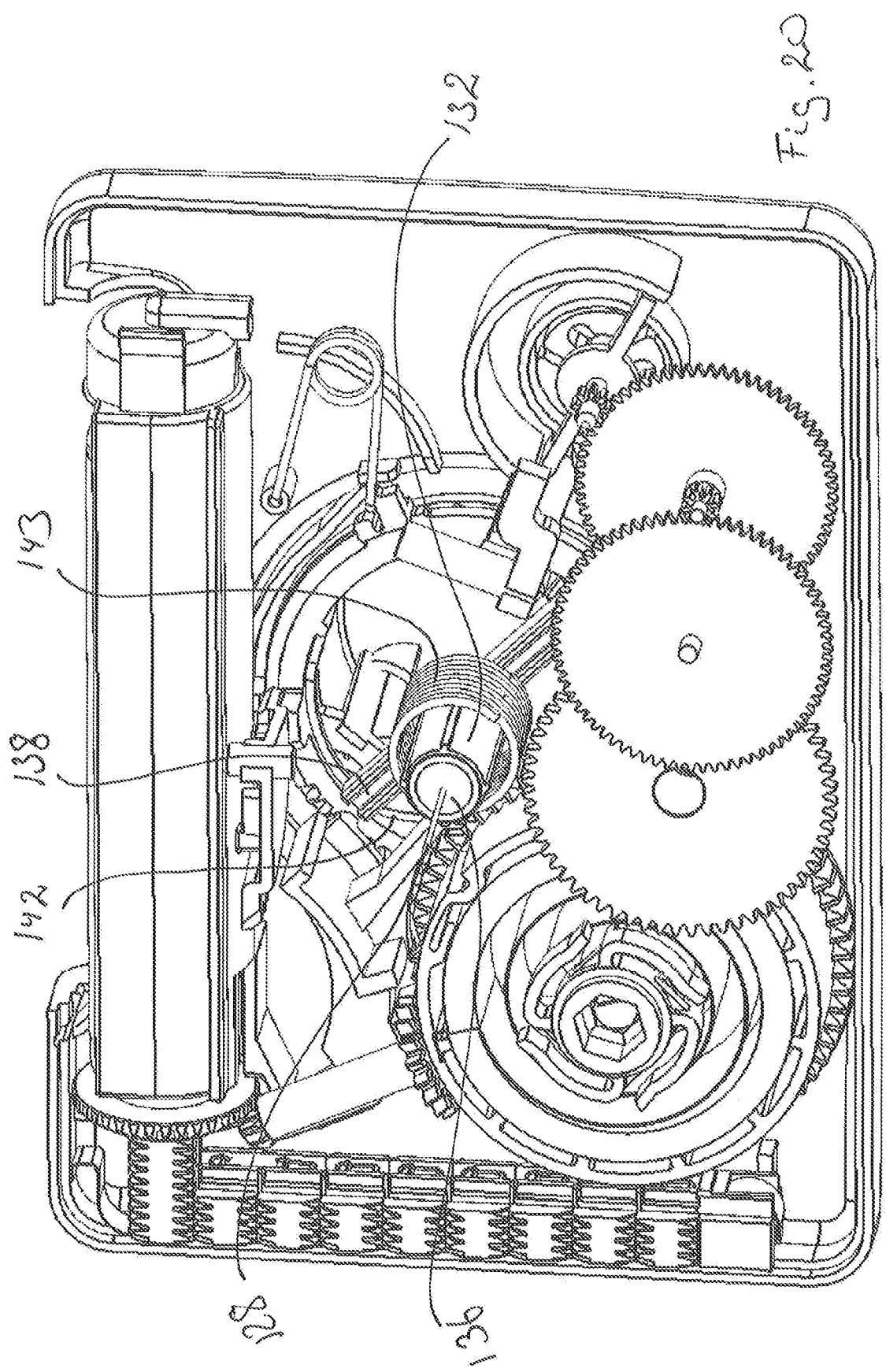

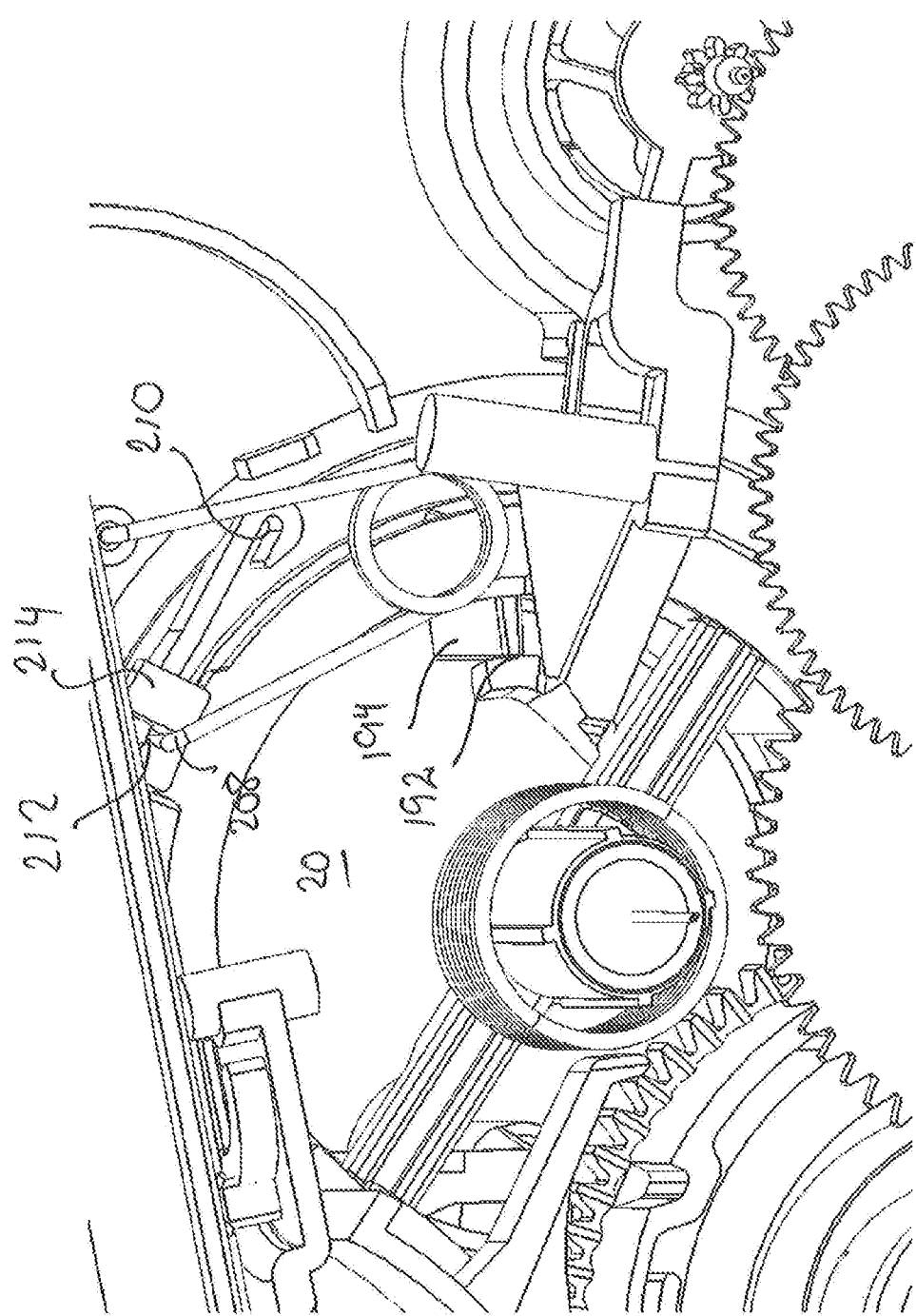

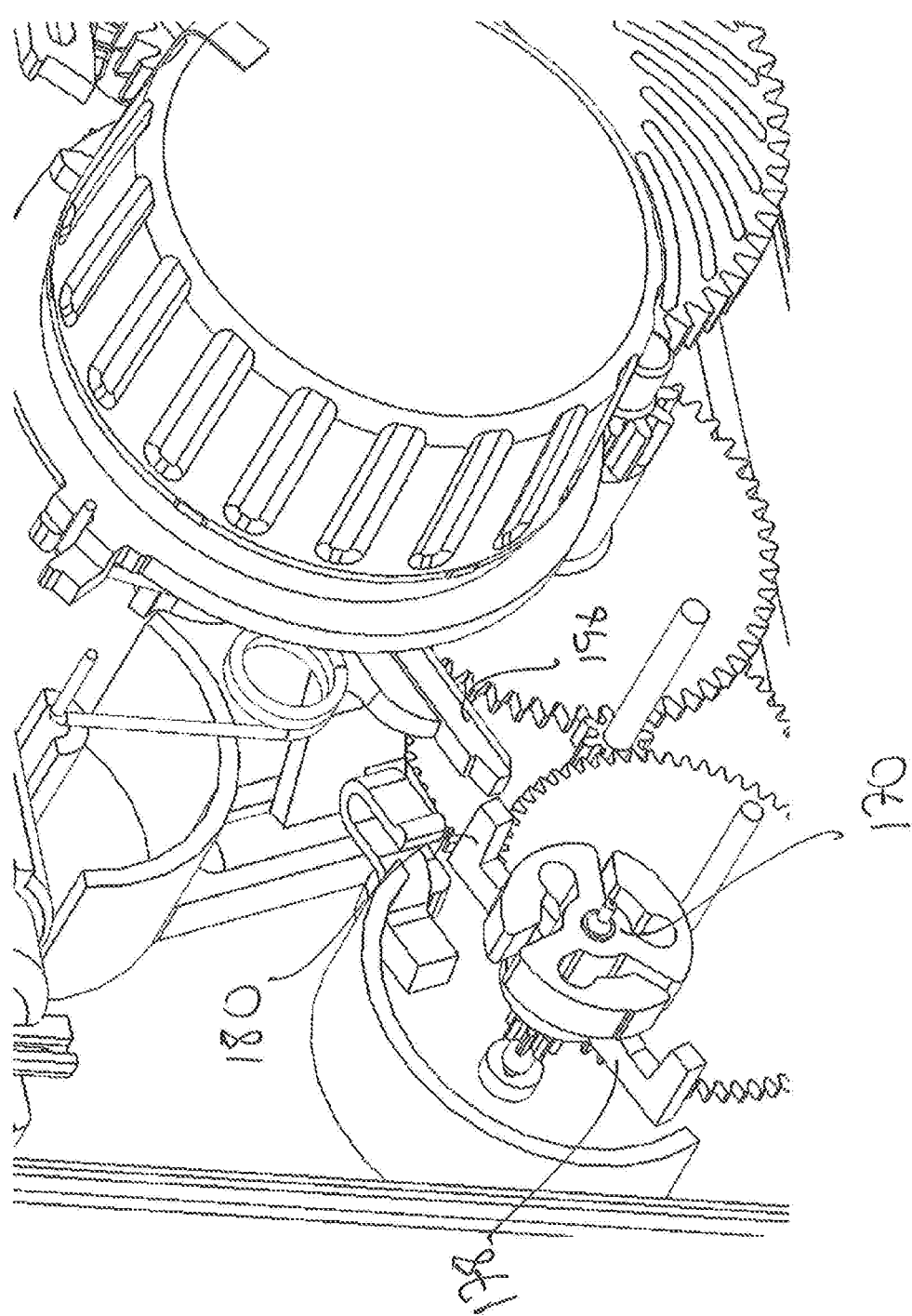

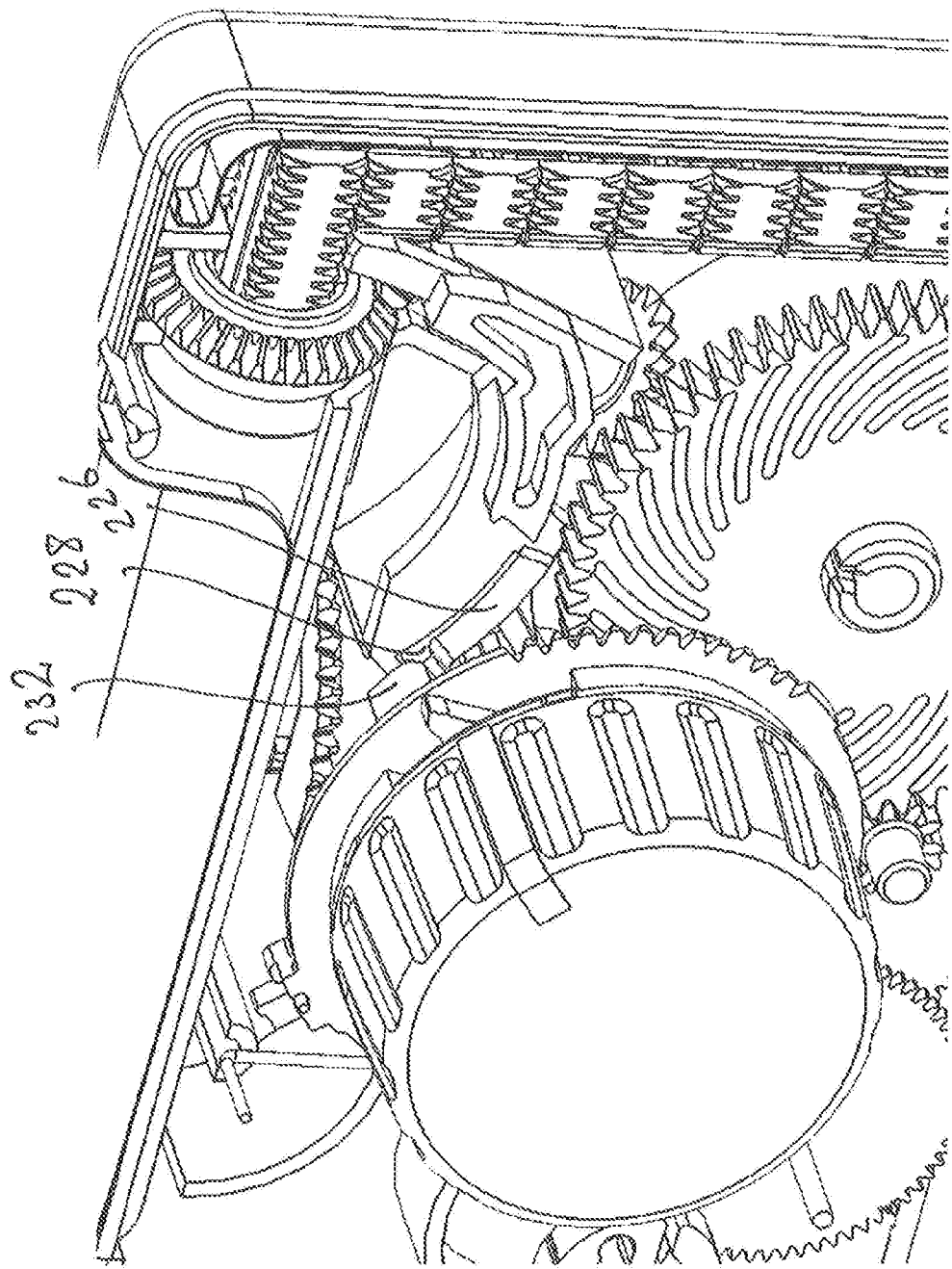

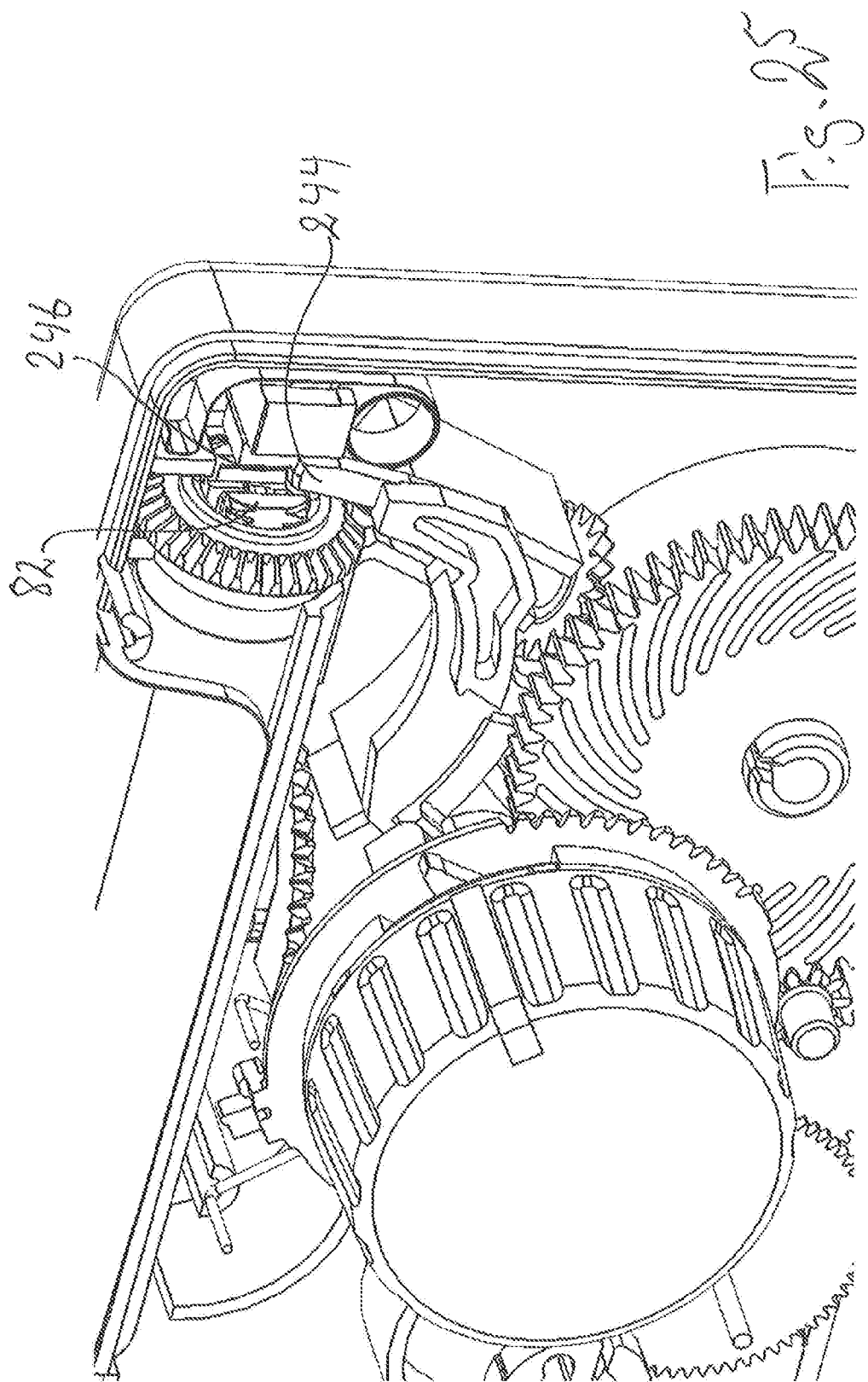

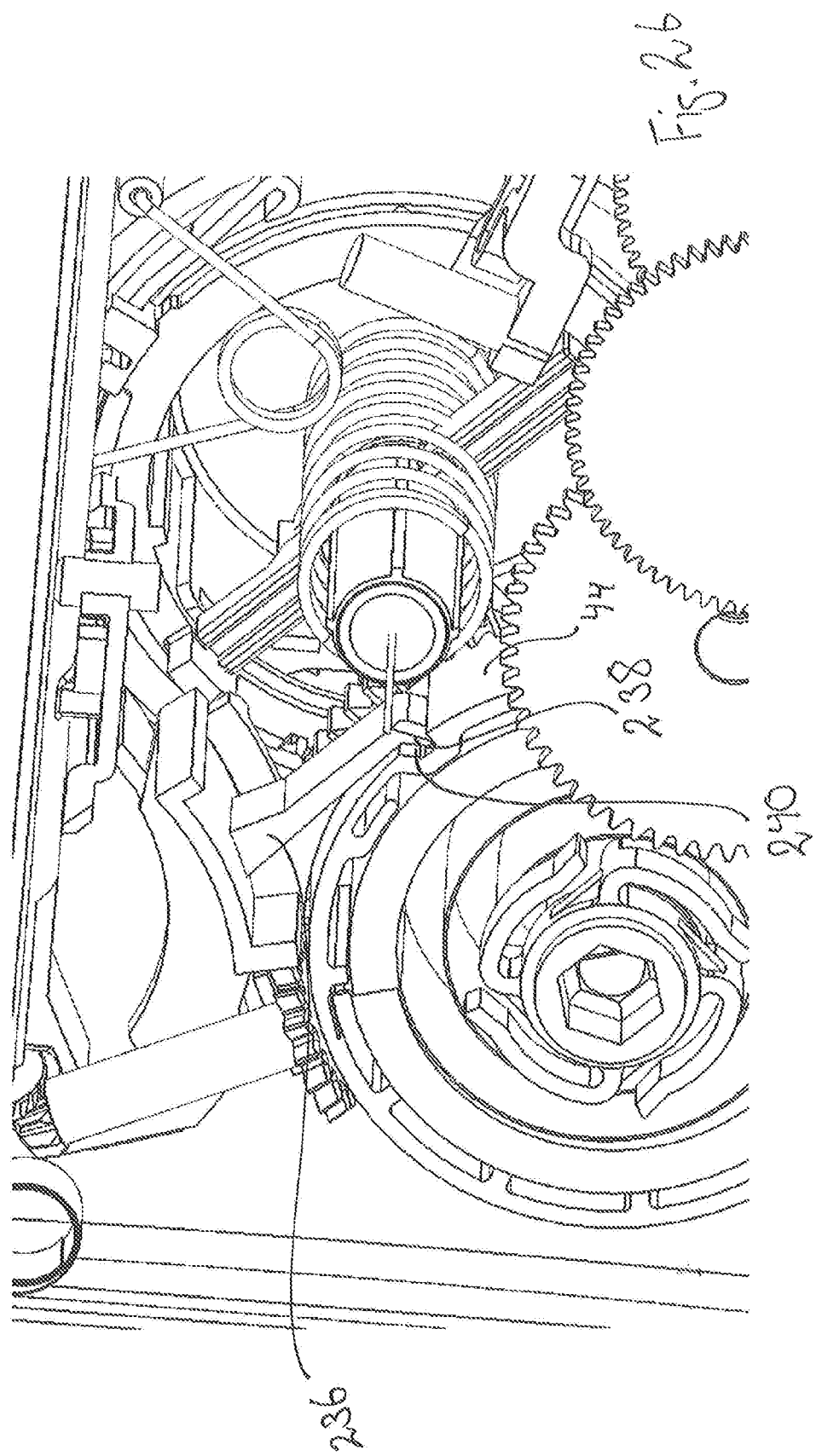

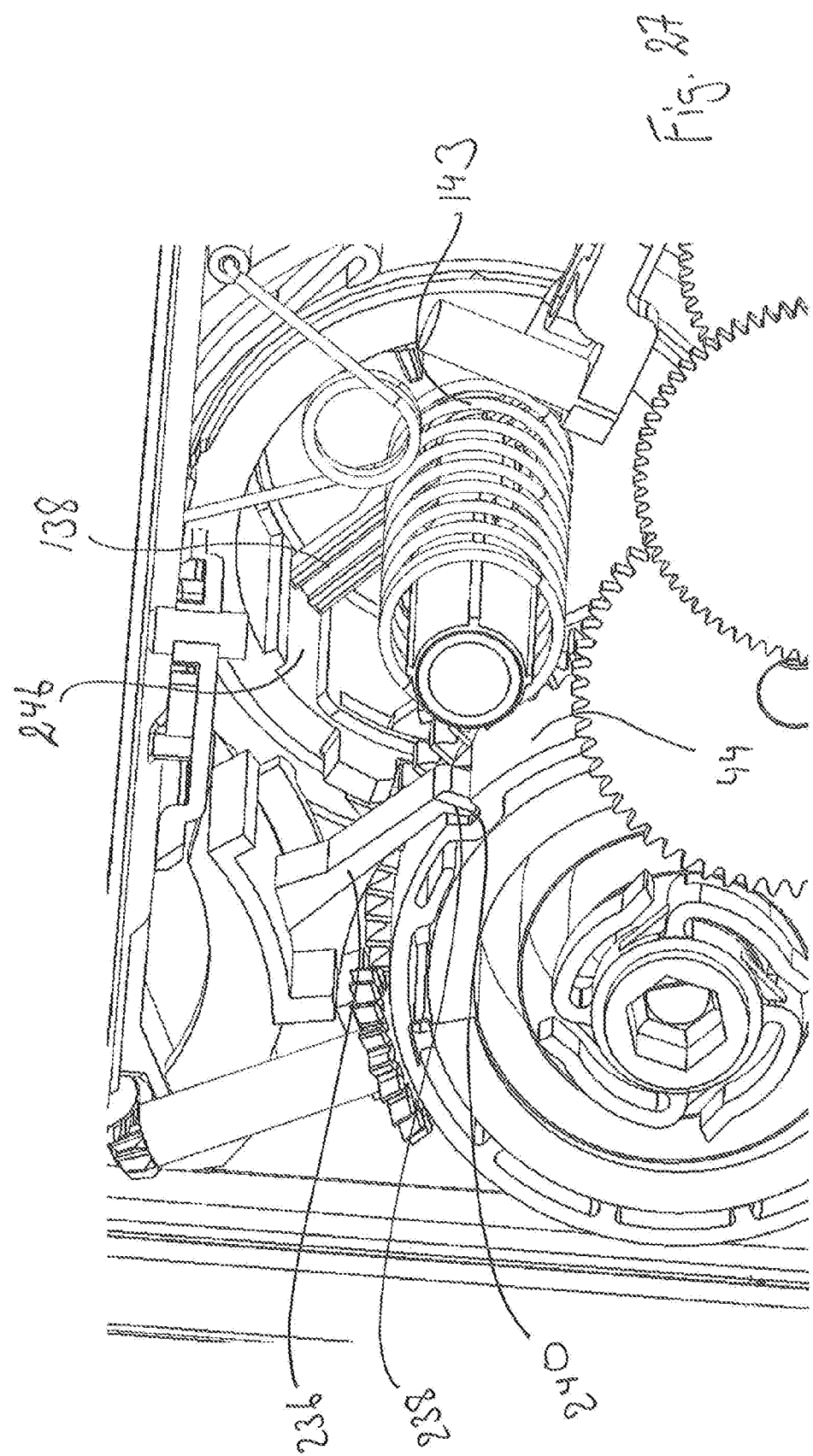

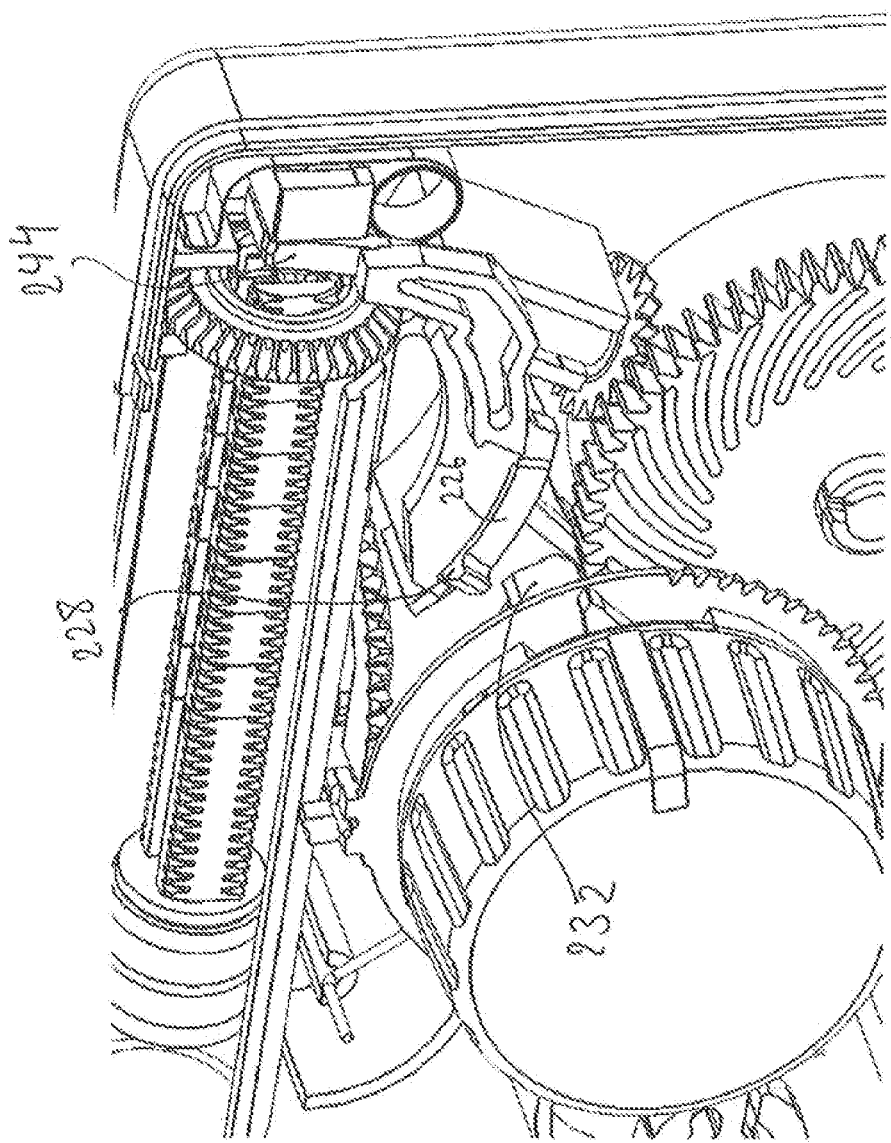

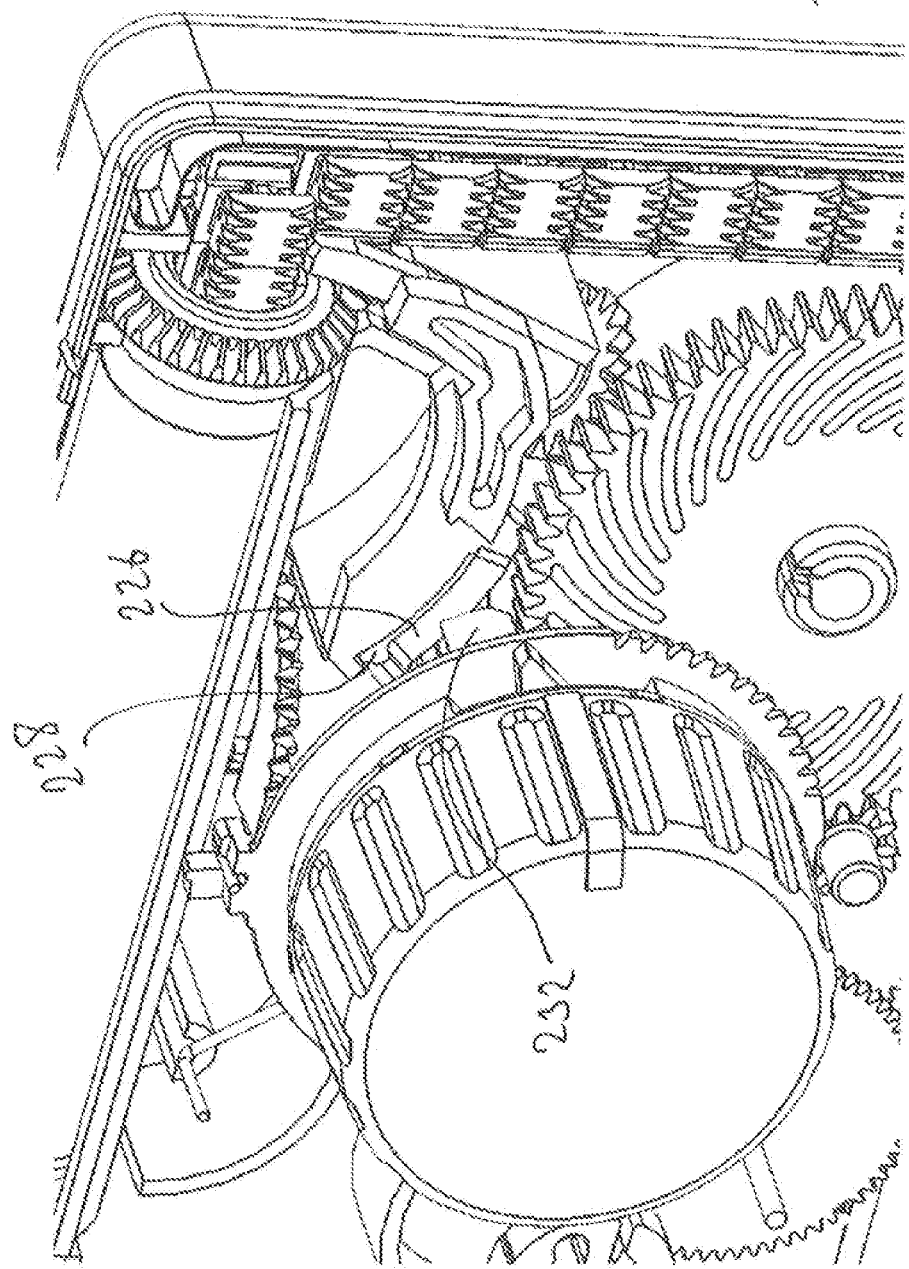

INFUSION DEVICE

CROSS REFERENCE TO RELATED APPLICATIONS

The present application is a continuation of U.S. patent application Ser. No. 14/391,947, filed Oct. 10, 2014, which is a U.S. National Phase Application pursuant to 35 U.S.C. § 371 of International Application No. PCT/EP2013/057326 filed Apr. 8, 2013, which claims priority to U.S. Provisional Patent Application No. 61/622,252, filed Apr. 10, 2012 and Swedish Patent Application No. 1250358-7 filed Apr. 10, 2012. The entire disclosure contents of these applications are herewith incorporated by reference into the present application.

TECHNICAL AREA

The present invention relates to an infusion device and in particular to a compact and easy to use mechanical driven infuser.

BACKGROUND

For a number of years infusers have been used that provides the patient or user with the means of administering a drug in an easy way without the need for a medically trained person, such as a physician or nurse to handle the device.

One drawback with these infusers is that they have a medicament container of a certain length as well as a plunger rod acting on said medicament container for delivering a dose of medicament, also having a certain length, whereby the total length of a device has to be at least the length of the medicament container and the plunger rod. If a drive member is used, such as for instance a drive spring, the length of the device is further increased.

One way of handling this is to make at least the plunger rod shorter or not adding so much to the overall length. One solution to this is to have a flexible plunger rod, which is disclosed for example in EP 1 583 573 where the plunger rod may be bent or formed as a circle. Another solution is disclosed in EP 1 276 529 having a bendable plunger rod with a ratchet on a side surface, where the plunger rod is bent around a cogwheel, for driving the plunger rod.

The drawback with these solutions is that the length may not be increased by the whole length of the plunger rod, but at least by some amount because the circle formed by the bent plunger rod also adds to the length. Further, the dimensions of the device in other directions are increased considerably by these solutions, providing a rather bulky device.

The above mentioned solutions utilize some sort of power spring wound around a shaft or the like positioned in the centre of the circle formed by the curved plunger rod. These power springs often act directly or almost directly on the curved plunger rod, such as with the device of EP 1 276 529 where the power spring acts on the cog wheel.

The drawback with this drive solution is that it complicates the addition of functions such as activation mechanisms, constant infusion speed mechanism, automatic stop mechanisms, just to mention a few. This is mainly because the plunger rod surrounds and thereby blocks access to the plunger drive spring without enlarging the device.

Regarding the infusion speed control aspect, some solutions have been device, such as for example in EP 1 326 659 where an electric motor is utilized for driving the flexible plunger rod. Also document WO 2010/112377 discloses a device utilizing electric motors for driving and controlling the movement and speed of the plunger rod.

The drawback with this is that the device has to rely on electric power in order to deliver a dose of medicament. If any batteries used are depleted, the device cannot be used at all, which may be critical for some types of drugs.

SUMMARY

The aim of the present invention is to remedy the above drawbacks with the state of the art devices.

According to one major aspect of the invention the piston plunger preferably comprises a number of distinct segments being inter-connectable to each other for forming an elongated piston plunger. In this aspect it is to be noted that the segments are not connected to each other beforehand. They are each distinct separate components that can be positioned inside the device in many ways.

The segments have members that provide a connection between the successive segments such that adding and connecting of segments forms an elongated piston plunger. This provides an advantage in that the space required for the plunger rod segments is much lesser than the space required for a flexible piston plunger. The interconnection of the segments preferably provides a locking in the longitudinal direction of the piston plunger, thereby acting as if it was a solid plunger rod.

The segments may be interconnected successively during delivery of a dose of medicament, whereby a subsequent segment is put in position and inter-connected with a previous segment as the piston plunger advances during infusion. This provides the possibility of arranging the segments in a pile or stack, in turn providing as very compact and space-saving design of the piston plunger. It is of course feasible to have more than one pile or stack of segments.

In order to advance and position subsequent segments of the piston plunger, especially when placed in a stack, a force member may be provided, capable of acting on said stack of piston plunger segments for successively interconnecting piston plunger segments. The force member may then act on the whole stack or pile, pushing on the last segment to be inter-connected so that each subsequent segment is pushed into place in relation to a previous segment. The force member may be a spring member or the like being in a tensioned state before activation of the infusion and the inter-connection of the segments.

Preferably the piston plunger is threaded and cooperates with a drive nut for the advancement of the piston plunger during infusion. In this aspect, the piston plunger segments are arranged with threads, designed to interact with the drive nut connected to said mechanical drive means.

An advantageous design of the piston plunger segments regarding both piling in stacks and interacting with a drive nut, the segments have a generally rectangular cross-section and having thread segments on the corners of the rectangles.

Further, in order to have a compact mechanical drive means, it may comprise a flat spiral spring preferably arranged in a rotatable spring housing. Thereby the length of the device is not affected by the mechanical drive means acting on the piston plunger. Rather, when a rotating spring housing is provided, a compact a drive member arranged between said spring housing and said drive nut may be arranged.

The device may further comprise an infusion speed control mechanism operatively connected to said mechanical drive means if that is a requirement. Preferably the infusion speed control mechanism comprises a centrifugal brake. The advantage with this is that a purely mechanical speed control may be obtained, thereby avoiding any electrically driven solutions. A mechanical centrifugal brake is also not so space-consuming and may be made very compact. In order to provide a proper function of the centrifugal brake, a transmission may be arranged between said mechanical drive means and said centrifugal brake.

Preferably the device may further comprise a penetration mechanism, capable of extending said infusion needle into an infusion site. Thereby the user does not necessarily have to perform the penetration manually, which is an advantage for some users who do not like the concept of needles and the penetration thereof. Then a penetration performed by the device is preferable. In addition to the penetration the penetration mechanism may further be capable of retracting said infusion needle upon completion of dose delivery. Then the device is harmless after performed infusion and the risk of unintentional needle sticks is removed.

The device may further be arranged with a manually operable operation mechanism, for activating delivery of a dose of medicament, such as a turnable knob, wherein turning of the knob a certain rotational distance activates the penetration mechanism. A turnable knob is an intuitive component that a user has no problems as how to handle. The turning motion of the knob may also be advantageous in that it may easily be transferred to other components of the device for initiating and/or performing additional functions, such as activating of infusion and withdrawal of the infusion needle.

These and other aspects of, and advantages with, the present invention will become apparent from the following detailed description of the invention and from the accompanying drawings.

BRIEF DESCRIPTION OF THE FIGURES

In the following detailed description of the invention, reference will be made to the accompanying drawings, of which FIG. 1 is a side view of an embodiment of the present invention, FIG. 2 is a side view of the device of FIG. 1 turned 180 degrees, FIG. 3 is an exploded view of the device of FIG. 1, FIG. 4 is a partly exploded view of the device of FIG. 1 with the proximal housing part removed for clarity, FIG. 5 is a partly exploded view of the device of FIG. 1 with the distal housing part removed for clarity, FIG. 7*a* is a detailed view of the piston plunger according to the invention with a spring unit and follower, FIG. 7*b* is a detailed view of a magazine to house the piston plunger, FIG. 8 shows a partly exploded view of the device according to FIG. 1, FIG. 9 shows a partly exploded view according to FIG. 8 and turned 180 degrees, FIG. 10 shows a partly exploded view of a penetration mechanism according to one aspect of the invention, FIG. 11 shows a further partly exploded view of the penetration mechanism, FIG. 12 show a perspective view of the device of FIG. 1 with the distal housing part removed for clarity, FIG. 13 shows a perspective view of the device of FIG. 1 with the proximal housing part removed for clarity, FIG. 14 shows a view of the distal housing part and a part of an operation mechanism, FIGS. 15*a, b* show details views of a knob comprised in the present invention, FIG. 16 shows a detailed view of a component comprised in an auto-stop mechanism, FIGS. 17 to 29 show different functional positions of the device during use.

DETAILED DESCRIPTION

Figure 6A:
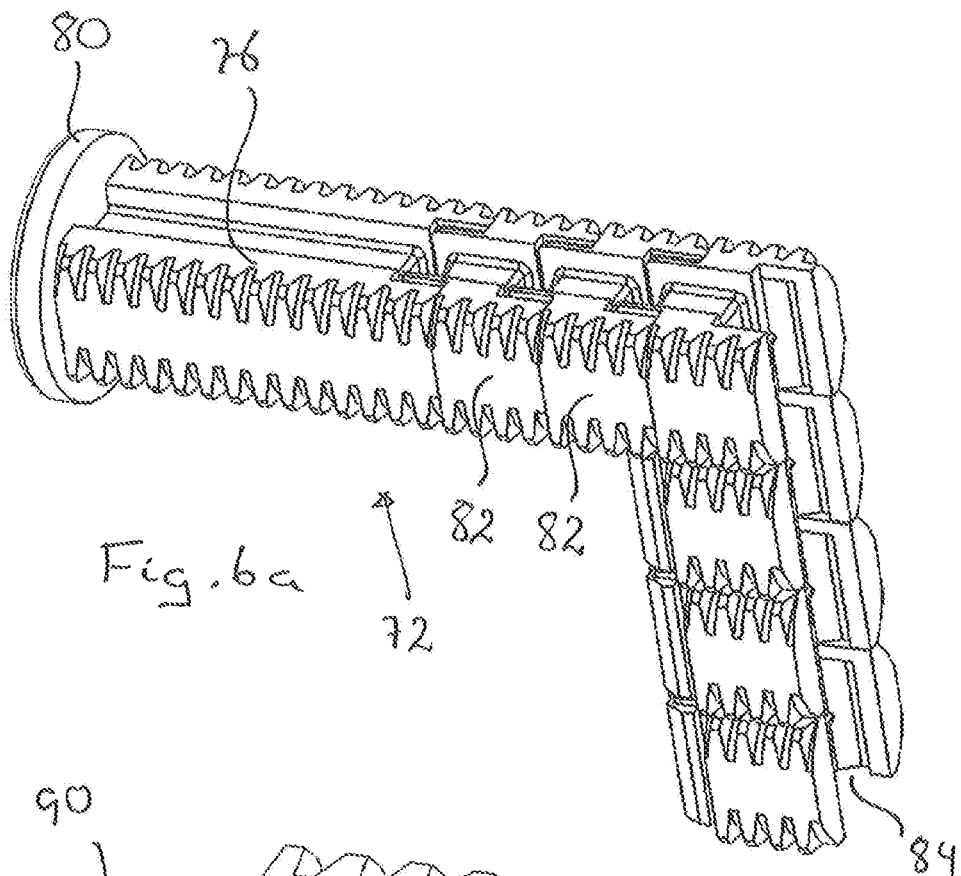
FIG. 6*a* is a detailed view of the piston plunger comprised in the present invention.

The embodiment of an infusion device shown in the drawings comprises a housing, which may be in two housing parts 10, 12. It is of course feasible that it comprises more than two housing parts. Preferably, the complete housing has a generally rectangular shape having a measure or thickness as seen along a proximal-distal axis 14 that is much less than the dimensions in the other two directions, vertical 16 and horizontal 18. The housing is arranged with an operating means, 20 in the embodiment shown as a turnable knob on the distally directed housing surface.

On the proximally directed housing surface, an opening is arranged, through which an Allen keyhole 22 is accessible, FIG. 2. The Allen keyhole 22 is arranged on a shaft 24, FIG. 4, rotatably arranged inside the housing and journalled with a distal end in a seat 26 on the inner surface of the distal housing part 10. A proximal end of the shaft 24 is arranged with a number of arms 28 that extend from a hub 30 in a generally circumferential direction. The free ends of the arms 28 are arranged with radially outwardly directed edges 32. The hub 30 with the arms 28 is intended to fit into a seat 34, FIG. 5, on the inner surface of the proximal housing part 10. The seat 34 is surrounded by an annular ledge 36 having radially inwardly directed teeth 38 of a certain configuration. The teeth 38 are intended to cooperate with the free ends of the arms 28 as will be described.

The shaft 24 is further arranged with a slit 40, FIGS. 4 and 5, along its length. Further, around the shaft 24 is a flat spiral spring 42, FIG. 4, wound, wherein the inner end of the spiral spring 42 fits into the slit 40, thereby locking the spring 42 to the shaft 24. The spring 42 is further arranged inside a spring housing 44 designed as a generally tubular part. The inner surface of the tubular part is arranged with a locking segment 46, FIG. 4, into which an outer end of the spiral spring 42 fits, thereby locking the spiral spring 42 to the spring housing 44. The spring housing 44 is further arranged with a sidewall 48, FIG. 5, having a central opening 50, through which the shaft 24 can extend. On the outer circumferential surface of the spring housing 44 a ratchet 52 is arranged. The ratchet 52 is intended to cooperate with a cogwheel 54 of a drive member 56, where the cogwheel 54 preferably is bevelled. The drive member 56 comprises a shaft 56 where the cogwheel 54 is attached to one end such that the shaft 56 extends generally in the radial direction of the spring housing 44 as seen in FIG. 4 along line 58. The shaft 56 is journalled in the proximal housing part 10 by support members 60, FIG. 5. A second cogwheel 62 is arranged at the second end of the shaft 56, FIG. 5. The second cogwheel 62 is arranged to be in contact with teeth 64 of a drive nut 66, where the teeth 64 extend around the circumference of the drive nut 66. The drive nut 66 is further arranged with a central opening 68, FIG. 4, which opening 68 is arranged with threads 70. The threads 70 of the drive nut 66 are intended to interact with a threaded piston plunger 72. The spring housing 44 is further arranged with indicia or markings 73, FIG. 5, in the embodiment shown a series of curved lines on the outer surface of the sidewall 48. These markings 73 are visible in a window or opening 75 on the distal housing part FIG. 1, as will be explained below.

Figure 6B:
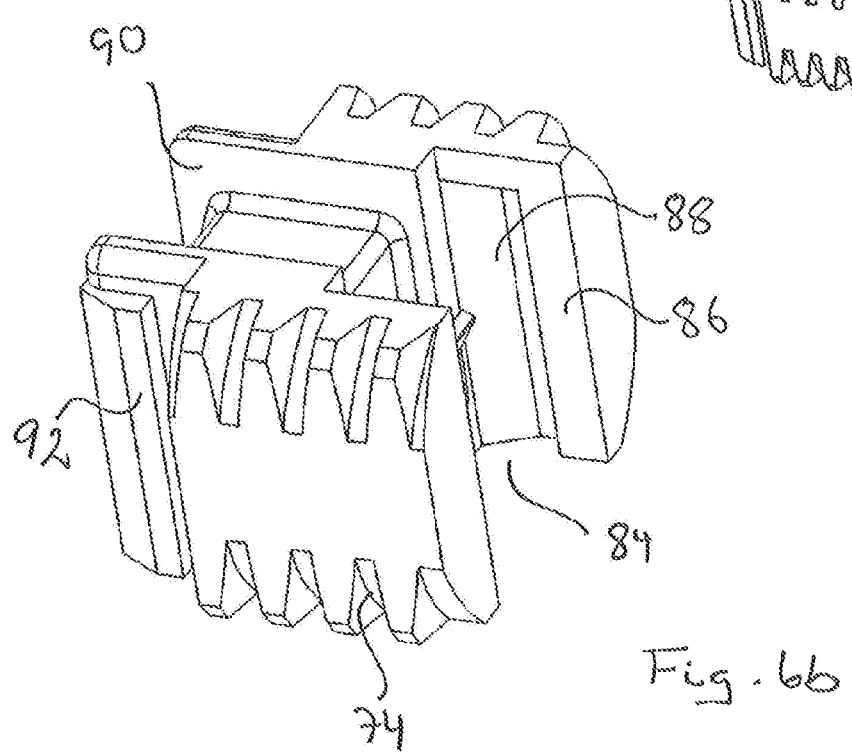
FIG. 6*b* is a detailed view of a piston plunger segment comprised in the piston plunger according to the present invention.

In the embodiment shown the piston plunger is of a certain configuration, FIG. 6a, b. The piston plunger generally has a rectangular configuration as seen in a cross-sectional view. Each corner of the rectangular piston plunger 72 is arranged with thread segments 74. Further the piston plunger is divided up into a number of piston plunger segments. The end of the first piston plunger segment 76 that is to be in contact with a medicament container 78, FIG. 3, is arranged with a generally circular pusher plate 80 having a diameter somewhat less than the inner diameter of the medicament container. The first piston plunger segment 76 has a certain length. The following piston plunger segments 82, FIG. 6a, are somewhat shorter. All piston plunger segments are arranged with connection members that comprise generally vertically arranged cut-outs 84 at their distal ends. The side walls 86 of the cut-outs 84 are arranged with generally vertically directed grooves 88, having a certain configuration. Further, each piston plunger segment apart from the first segment, is arranged with a proximally directed nose 90 designed to fit into the cut-out 84 of a previous plunger segment 82. Further the nose 90 is arranged with generally vertically extending ledges 92 having similar configuration as the grooves 88 of the cut-out 84, whereby the ledges 92 may fit into the grooves 88 as seen in FIG. 6b.

The piston plunger segments 82 are arranged in a generally vertical stack on top of each other and directed such that the corners with the thread segments extend generally horizontally, FIG. 7a. The stack of piston plunger segments is held in place inside the housing by a magazine 94 providing side supports on three sides. The fourth side is arranged with an elongated slit 96, FIG. 7b. In the slit a flat band spring 98 is arranged having a first upper end attached to a fixture post 100 on the magazine 94, FIG. 7a. The second lower end is attached to a piston plunger follower 102 inside that magazine 94, FIG. 7a. The function of the described components will be explained below.

The proximal end of the piston plunger 72 extends into a space in the device intended to accommodate the medicament container 78, FIG. 8. The space is accessible via a hingedly attached lid 104, FIG. 1, on an upper area of the housing. Inside the space a holder or cartridge retainer 106, FIG. 3, 11, is arranged, on which the medicament container may be placed. The cartridge retainer 106 is arranged slidable in a longitudinal direction inside the housing guided by its longitudinal edges 108, FIGS. 8 and 9, fitting into guides 110 on each housing part, FIG. 8. Further a cogwheel segment 111 of a cartridge cam 112, is turnably attached to posts 114, FIG. 9, on the proximal housing part 12. An upper surface of the cartridge cam 112 is arranged with a curved ridge 116, FIG. 9, which ridge cooperates with downwardly directed protrusions 118 on the underside of the cartridge retainer 106. The cogwheel segment 111 of the cartridge cam 112 is further connected to a ratchet segment 120, FIG. 9, arranged on an outer surface of the operation member 20, in the embodiment shown a turnable knob. The function of the knob and the cartridge cam will be explained in detail below.

The cartridge retainer 106 is further arranged with an end piece 122, FIG. 9, which is intended to be in contact with an end of the container 78, comprising a septum (not shown). The end piece 122 is further arranged with a hollow needle piece 124, FIG. 9, intended to pierce the septum of the container, as will be described. The needle piece 124 extends through the end piece and is further provided with a bend of generally ninety degrees. At the lower end of the needle piece, a first end of a flexible tube 126 (not shown) is attached. Further, a second end of the flexible tube is attached to a distal end of an infusion needle 128, FIG. 10. The infusion needle is attached to a generally cylindrical needle hub 130, which in turn is positioned inside a generally cylindrical needle plunger 132. The needle plunger 132 is in turn positioned inside a generally tubular guide piece 134, being a part of the proximal housing part 10. A lower end of the guide piece is open towards the proximal direction and the opening is arranged with a ruptable membrane 136. The needle plunger 132 is further arranged with transversally extending arms 138, FIGS. 10 and 11. Each arm is arranged with a chamfered side surface 140, which chamfered surfaces 140 are intended to cooperate with ledges 142, FIG. 5, on an inner surface of the knob 20. The needle plunger 132 is urged in the distal direction by a spiral spring 143 acting between the transversal arms 138 and the inner surface of the proximal housing part, FIG. 10.

The device is further arranged with an infusion speed control mechanism 144, that preferably is capable of providing a constant infusion speed during the infusion. It comprises a transmission, FIGS. 12 and 13, with a first cogwheel 146, FIG. 12, with a small diameter acting on the ratchet 52 on the outer surface of the spring housing 44. The first cogwheel 146 is attached to a second cogwheel 148 having a larger diameter, wherein the first and second cogwheels 146, 148 are rotatably arranged to a first shaft 150. The second cogwheel 148 is in engagement with a third cogwheel 152 having a smaller diameter. The third cogwheel 152 is attached to a fourth cogwheel 154 having a larger diameter. The third and the fourth cogwheel 152, 154 are rotatably arranged to a second shaft 156. The fourth cogwheel is then in engagement with a fifth 158 cogwheel having a smaller diameter, FIG. 13. The fifth cogwheel 158 is attached to a sixth cogwheel 160 having a larger diameter. The fifth and the sixth cogwheels 158, 160 are rotatably arranged to a third shaft 162. The sixth cogwheel 160 is in engagement with a seventh cogwheel 164. The seventh cogwheel 164 is attached to a centrifugal brake 166, comprising a number of arms 168 attached to a hub 170, FIG. 12, where the seventh cogwheel 164 and the hub 170 are rotatably arranged to a fourth shaft 172. The arms 168 of the centrifugal brake 166 extend generally in circumferential direction, having their free ends becoming trailing ends when the hub rotates. The outer surfaces of the arms 168 are arranged with ledges 174. The hub 170 with its arms 168 is positioned in a generally tubular piece 176 attached to the inner surface of the distal housing part 12. The diameter of the tubular piece 176 is chosen such that there is a small gap between the ledges 174 of the arms 168 and the inner surface of the tubular piece 176 when the hub 170 is not rotating. The centrifugal brake 166 is further arranged with transversally extending arms 178 attached to the hub 170. The free ends of the arms 178 are arranged with end pieces 180, FIG. 14, extending generally perpendicular to the extension of the arms 178.

The device is further arranged with an operation mechanism 182. The operation mechanism 182 comprises the previously mentioned knob 20, FIG. 14. Further, it comprises a start linkage 184 designed with an arm 186 attached to a cylindrical hinge 188 fitting into a post 190 in the proximal housing part 10. The arm 186 extends towards and into the knob 20. At the end of the arm a contact surface 192 is arranged, which is intended to interact with a protrusion 194 inside the knob 20, as will be explained. Further the arm 186 of the start linkage 184 is arranged with a branch 196 extending towards the centrifugal brake 166, and intended to interact with the end pieces 180 of the transversal arms 178 of the hub 170. At an inner end of the arm 186 a spring element 198 is arranged.

The operation mechanism is further arranged with a movement member arranged as a spring 200 provided with two arms 202, 204, each in turn arranged with an end piece 206, 208 directed generally perpendicular to the arms 202, 204. The first end piece 206 of the spring is attached to the distal housing part, FIG. 12. The second end piece is in an initial position held by a hook 210, FIG. 12, adjacent the opening in the distal housing part intended for the knob 20. When the knob is operated during use, as will be described, the second end piece will fit into a seat 212 in a generally radially protruding ledge 214 attached to the knob, FIG. 15.

The device is further arranged with an auto-stop mechanism 216, FIG. 11. It comprises a beam 218 provided with a proximal end 220, FIG. 15. The proximal end 220 is arranged with a downwardly directed ledge 222, intended to be in sliding contact with a curved surface 224, FIG. 12, on the inner surface of the proximal housing part 10. Further a flexible arm 226 is arranged on a side surface of the beam 218, the arm 226 being flexible in the proximal-distal direction 14. The arm 226 is arranged with a distally directed ledge 228, the ledge being provided with a bevelled surface 230. The arm 226 and the ledge 230 are arranged to come in contact with a proximally directed protrusion 232 on the knob 20, FIG. 15. The protrusion of the knob is also arranged with a bevelled surface 234, intended to interact with the bevelled surface 230 of the arm 210 of the beam 202, as will be explained. Further, the proximal part of the beam 218 is arranged with an arm 236 extending from the underside of the beam 218 and towards the spring housing 44 as seen in FIG. 13. The free end of the arm 236 is arranged with a downwardly directed protrusion 238, which protrusion 238 is intended to interact with a groove 240, FIGS. 4 and 13, arranged on the outer surface of the spring housing 44, as will be explained.

The beam 218 is arranged with a distal part 242 being directed more upwards than the proximal part as seen in FIG. 12, giving the beam a curved shape as seen in the proximal direction of the device. The upper end 244 of the distal end of the beam 218 is positioned adjacent the drive nut 66 and the piston plunger 72, FIG. 12, for reasons that will be explained below.

Intended Function of the Device

The device is usually delivered without a medicament container. Thus, before use, a medicament container 78 has to be inserted into the device. The lid 104 at the upper end of the device is then opened, FIG. 17, whereby the space and the cartridge retainer 106 are accessible. The medicament container 78 is then inserted with a neck portion towards the end piece 122 of the cartridge retainer 106. The lid is then closed.

The device is now made ready. This may be done by inserting an allen key into the hole 22 on the proximal surface of the device and turning the shaft 24 in the anti-clockwise direction. This causes the arms 28 of the hub 30 to slide over the teeth 38 because of the direction of the arms in relation to the teeth. Because the inner end of the spiral spring is attached to the turning shaft 24 the spiral spring is tensioned. When the user stops turning the shaft, it is locked against rotating back because of the edges 32 of the arms now locking against the teeth 38. The device is now ready for delivering a dose of medicament.

In the initial position, the knob is in the rest or delivery position as seen in FIG. 17. In this position, as seen in FIG. 128, the ratchet segment 120 of the knob 20 is not yet in engagement with the cartridge cam. The contact surface 192 of the operation mechanism 182 is on the inner surface of the knob, unaffected. As seen in FIG. 19, this position of the operation mechanism causes the branch 196 to be in the path of the end pieces 180 of the arms 178 of the hub 170, whereby rotation of the hub 170 of the constant speed control mechanism 144 is prevented. The process up to this point may be done without the device being in contact with the patient. In order to be able to deliver a dose of medicament to the patient, the proximal surface of the device has to be in contact with some part of the body of the patient, i.e. to releasibly attach the device to the body. This may be performed in many ways, by straps, by merely pressing it manually, but preferably the proximal surface is arranged with some sort of adhesive, like sticky tape, with which the device may be fastened to the body. One variant is to have double-sided sticky tape on the proximal surface with an outer protective layer that is peeled off before attachment.

When the device is activated, the user initially turns the knob to the first position, as seen in FIG. 1, displaying the pause sign. This turning of the knob causes its ratchet segment 120 to engage the cogwheel segment 111 of the cartridge cam, whereby the cartridge cam is turned around its contact point with the proximal housing part. The turning of the cartridge cam causes in turn the curved ridge 116 to act on the protrusions 118 of the cartridge retainer 106, causing the cartridge container 106 to be moved linearly, guided by the guides for the cartridge retainer 110, such that the end piece 122 is moved towards, and in contact with, the neck portion of the medicament container 78. The medicament container 78 is in turn held in longitudinal position by the proximal end of the piston plunger 72 with the pusher plate 80 being in contact with the stopper of the medicament container. The movement of the end piece causes the needle piece 124 to penetrate the septum of the medicament container, thereby creating a passage for the medicament through the septum. The medicament can now flow into the flexible tube and to the infusion needle.

The turning of the knob also initiates the penetration by the infusion needle. The ledges 142 on the inner surface are inclined, as seen in FIG. 20 and in FIG. 15, and the chamfered surfaces 140 of the transversal arms 138 of the needle plunger 132, will slide on these inclined surfaces, whereby the needle plunger 132 is pushed in the proximal direction against the force of the needle plunger spring 143. The infusion needle will rupture the membrane 136 and extend out of the device as shown in FIG. 20.

Initiation of Infusion

Figure 21:
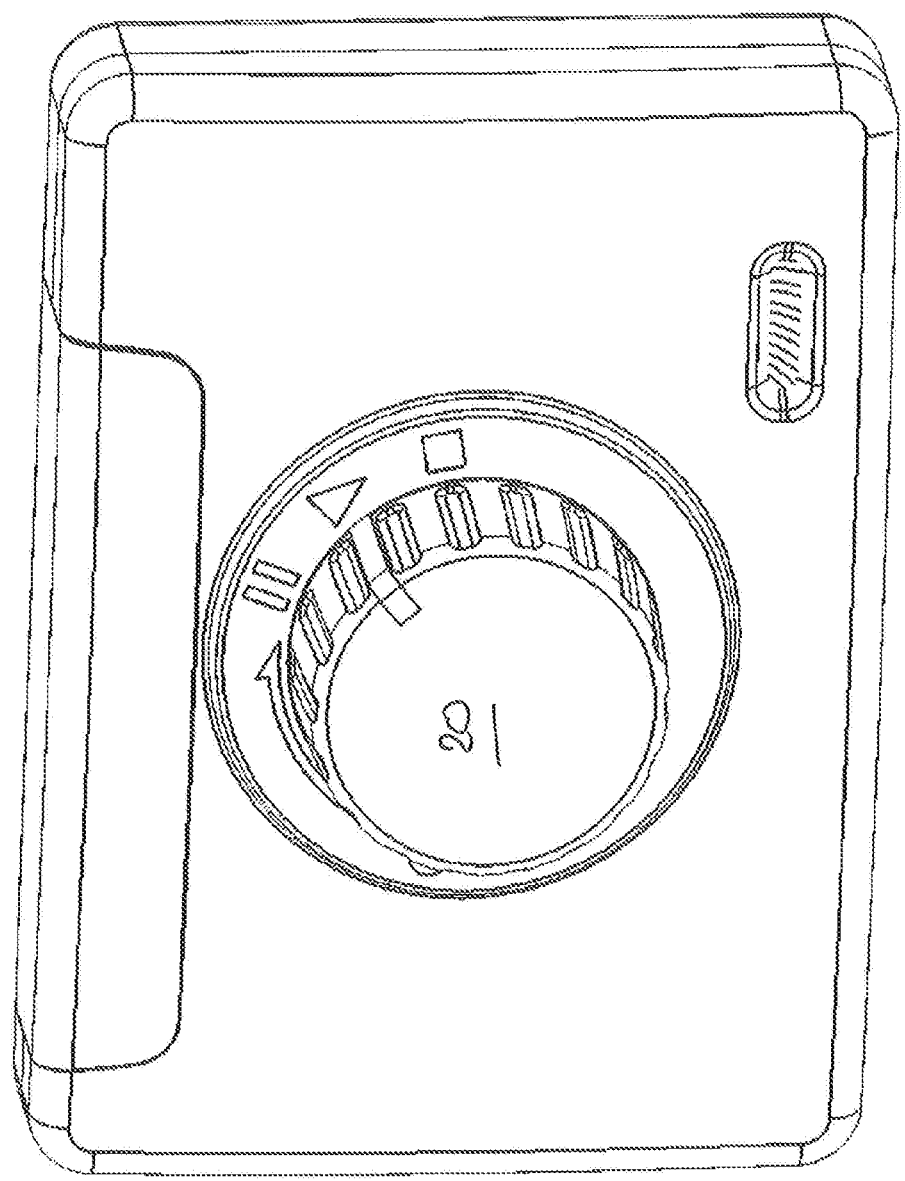

In order to start the infusion, the user turns the knob a step further to the position indicated by a "play" arrow, FIG. 21. This causes the protrusion 194 inside the knob 20, FIG. 22, to come in contact with the contact surface of the start linkage 184, whereby it will turn around its hinge 188. The turning of the start linkage will cause the branch 196 to move out of contact with the end pieces 180 of the arms 178 of the hub, whereby the hub is free to rotate, FIG. 23. Because of the chain of cogwheels of the transmission of the speed control mechanism, the spring housing 44 is free to rotate due to the force of the tensioned flat spiral spring 42. The knob is held in this position in that the end piece of 208 of the spring during rotation is moved from the hook 210 to the seat 212 of the ledge 214 of the knob 20, FIG. 22. This new position of the spring will urge the knob to turn in this direction. However, the knob is prevented from turning further because the protrusion 232 of the knob 20 with its bevelled surface 234 is in contact with the bevelled surface 230 of the ledge 228 of the flexible arm 226, FIG. 24.

Infusion Operation

The rotation of the spring housing 44 will cause its ratchet 52 to move around the circumference, thereby acting on the cogwheel 54 of the drive member. The rotation of the second cogwheel 62 of the drive member 54 will, due to the engagement with the drive nut 66, cause the latter to rotate. In turn, the rotation of the drive nut 66 will cause the piston plunger 72 to move in the proximal direction by the engagement between the drive nut and the thread segments 74. When the first piston plunger segment 76 has moved a distance in the proximal direction, the space behind the first segment is so large that a subsequent piston plunger segment 82 may be pushed in the vertical direction by the flat band spring 98 acting on the lowermost positioned piston plunger follower 102. When the following piston plunger segments are pushed upwards in the vertical direction, they are connected to a previous piston plunger segment in that the ledges 92 of the nose 90 of the subsequent segment fit into the grooves 88 of the cut-out 84 of the previous segment, thereby sequentially "building" a continuous piston plunger 72 with the segments. The process of the infusion sequence is also visible in the opening 75 where the indicia 73 on the spring housing 44 pass Speed Control of Infusion The movement of the piston plunger 72 in the proximal direction will cause the stopper of the medicament container to move inside the container, whereby medicament is pushed through the needle piece 124, the flexible tube 126 and the infusion needle 128. A constant speed of the piston plunger 72 is ascertained by the constant speed control mechanism in that the rotation of the spring housing 44 is transmitted to the hub 170 of the centrifugal brake 166 via the transmission of cogwheels 146, 148, 152, 154, 158, 160 and 164. The rotation of the hub 170 will cause the arms 168 to move in the radial direction if the speed is increased over a pre-set level. The movement in the radial direction will cause the ledges 174 of the arms 168 to be moved in contact with the tubular piece 176, causing a contact friction between the ledges of the arms and the tubular piece that will reduce the speed. In this manner the speed will be kept more or less constant when the arms are moved in and out of contact with the tubular piece during rotation.

Pausing of the Infusion

The user may pause the infusion by turning the knob 20 back to the "pause" position against the force of the spring 200. This will cause the contact surface 192 of the start linkage 184 to move out of contact with the protrusion 194 of the knob, which in turn will cause the start linkage to swing back to its initial position by the spring element 198. This in turn will cause the branch 196 to move in the path of the end pieces 180 of the arms 178 of the hub 170, whereby the rotation of the hub is blocked. This in turn will stop the rotation of the spring housing 44 via the transmission, and also the rotation of the drive nut, thereby stopping the movement of the piston plunger 72.

Auto-stop Function

When the infusion sequence is about to end when the medicament container has been emptied, there will be a space 246 behind the last of the piston plunger segments 82, FIG. 25. Because the upper end 244 of the beam constantly has been in contact with and underside of the piston plunger, it is now free to move upwards into the space. Due to this and the form of the beam, the arm 236 is moved towards the spring housing, whereby the protrusion 238 of the arm 236 comes in contact with the outer surface of the spring housing 44 and when the groove 240 of the spring housing comes in position in relation to the protrusion, the latter will be forced into the groove and the rotation of the spring housing is blocked, FIG. 26.

When the protrusion 238 enters the groove 240 the force of the spiral spring on the spring housing will cause the beam to be lifted somewhat in the vertical direction. This movement of the beam will cause the flexible arm 226 and its ledge to be moved out of contact with the protrusion of the knob 232 FIG. 27. Due to the force of the spring 200 acting on the knob 20 and urging it in the clock-wise direction, the knob will be turned in this direction. On the inner surface of the knob, the ledge that the transversal arm is resting on is terminated at 246, FIGS. 27 and 15b, whereby the needle plunger is free to be moved in the distal direction by the needle plunger spring 143. This now causes the infusion needle to be withdrawn from the infusion site. The device may now be removed and discarded.

Manual Stop

Instead of the automatic stopping of the device, it may be stopped manually by turning the knob further, FIG. 1, against the force between the flexible arm 226 and the protrusion 232 of the knob, FIG. 28. This will cause the flexible arm 226 to move in the proximal direction such that the protrusion 232 of the knob can pass. The arm will then flex back whereby the ledge 228 of the arm 226 prevents the user from turning back the knob. At the same time, the contact surface 192 of the start linkage 184 is moved out of contact with the protrusion 194 of the knob, which will stop the rotation of the spring housing 44 via the transmission in the same manner as when the infusion is paused as described above. However, in this position, the knob may not be turned back, thereby avoiding unintentional activation of the device again. Further, in this position, the ledge that the transversal arm is resting on is terminated, whereby the needle plunger is free to be moved in the distal direction by the needle plunger spring, in the same manner as with the auto-stop function. This now causes the infusion needle to be withdrawn from the infusion site. The device may now be removed and discarded.

It is to be understood that the embodiment described above and shown in the drawings is to be regarded only as a non-limiting example of the invention and that it may be modified in many ways within the scope of the patent claims.

The invention claimed is:
1. An medicament delivery device, comprising:
a housing;
a compartment having a longitudinal axis and positioned inside the housing for holding a medicament container;
a needle connected to a flexible tube and movably arranged within the housing and in fluid communication with the medicament container through the flexible tube for delivering a dose of medicament, where the needle has a proximal end that moves from a first position within the housing to a second position that is extended to a position outside the housing, where the movement of the needle from the first position to the second position defines an axis of movement;
a piston plunger disposed in the housing for acting on the medicament container to deliver the dose of medicament, wherein the piston plunger moves parallel to the longitudinal axis of the compartment in a direction that is transverse to the axis of movement of the proximal end of the needle; and a driver operatively engaged with the piston plunger to deliver the dose of medicament;

wherein when the medicament device is activated, the proximal end of the needle moves to the second position before delivering the dose of the medicament.

2. The medicament delivery device of claim 1 further comprising a needle hub fixed to a distal end of the needle, where the needle hub moves in a direction transverse to the movement of the piston plunger.

3. The medicament delivery device of claim 1 further comprising an end piece connected to a container needle, where the end piece is positioned adjacent to the compartment such that the container needle engages the medicament container to establish a fluid communication with the medicament.

4. The medicament delivery device of claim 3, further comprising the flexible tube connected with both the container needle and the needle such that the dose of medicament flows from the medicament container to the proximal end of the needle during delivery of the dose of medicament.

5. The medicament delivery device of claim 1, where the needle when in the second position is locked relative to the housing to prevent movement in a distal direction.

6. The medicament delivery device of claim 1 further comprising a biasing member operatively associated with the needle hub to move the needle relative to the housing.

7. The medicament delivery device of claim 1, further comprising an injection speed control mechanism operatively connected to the driver.

8. The medicament delivery device of claim 7, where the injection speed control mechanism comprises cogwheels.

\* \* \* \* \*